(12) United States Patent
Mikos et al.

(10) Patent No.: US 9,532,875 B2
(45) Date of Patent: Jan. 3, 2017

(54) COMBINED SPACE MAINTENANCE AND BONE REGENERATION SYSTEM FOR THE RECONSTRUCTION OF LARGE OSSEOUS DEFECTS

(71) Applicant: WILLIAM MARSH RICE UNIVERSITY, Houston, TX (US)

(72) Inventors: Antonios G. Mikos, Houston, TX (US); Mark E. Wong, Houston, TX (US); Simon W. Young, Houston, TX (US); James D. Kretlow, Houston, TX (US); Meng Shi, Katy, TX (US); F. Kurtis Kasper, Houston, TX (US); Patrick Spicer, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 110 days.

(21) Appl. No.: 14/491,681

(22) Filed: Sep. 19, 2014

(65) Prior Publication Data
US 2015/0081034 A1    Mar. 19, 2015

Related U.S. Application Data

(60) Division of application No. 13/548,385, filed on Jul. 13, 2012, now abandoned, which is a
(Continued)

(51) Int. Cl.
*A61F 2/28* (2006.01)
*A61L 27/16* (2006.01)
(Continued)

(52) U.S. Cl.
CPC ............... *A61F 2/28* (2013.01); *A61L 27/16* (2013.01); *A61L 27/3608* (2013.01); *A61L 27/56* (2013.01);
(Continued)

(58) Field of Classification Search
CPC ...................... A61F 2/2803; A61F 2210/0085
See application file for complete search history.

(56) References Cited

U.S. PATENT DOCUMENTS 5,204,382 A * 4/1993 Wallace ............... A61L 27/10
424/423
2005/0043813 A1   2/2005 Kusanagi
(Continued)

OTHER PUBLICATIONS

Alain C. Masquelet, MD. et al., The Concept of Induced Membrane for Reconstruction of Long Bones, Orthopedic Clinics of North America, vol. 41, Jan. 2010, pp. 27-37.*
(Continued)

*Primary Examiner* — Brian Dukert
(74) *Attorney, Agent, or Firm* — Reed Smith LLP; Robert R. Riddle; Matthew S. Gibson

(57) ABSTRACT

Systems, methods and compositions useful for treatment of traumatic bone injuries are provided. In one embodiment, a bone reconstruction system comprising a space maintaining composition comprising porous polymethylmethacrylate; and an osseous generating construct comprising a polymethylmethacrylate chamber that comprises one or more osseous generating materials is provided. Associated compositions and methods are also provided.

9 Claims, 19 Drawing Sheets

Related U.S. Application Data continuation-in-part of application No. PCT/US2011/021266, filed on Jan. 14, 2011.

(60) Provisional application No. 61/295,478, filed on Jan. 15, 2010.

(51) Int. Cl.
*A61L 27/36* (2006.01)
*A61L 27/56* (2006.01)

(52) U.S. Cl.
CPC ...... *A61F 2/2803* (2013.01); *A61F 2210/0085* (2013.01); *A61L 2430/02* (2013.01)

(56) References Cited

U.S. PATENT DOCUMENTS

| | | |
|---|---|---|
| 2005/0100578 A1 | 5/2005 | Schmid et al. |
| 2006/0083730 A1 | 4/2006 | Kusanagi et al. |
| 2008/0206308 A1 | 8/2008 | Jabbari et al. |
| 2009/0081276 A1 | 3/2009 | Alsberg et al. |
| 2009/0148497 A1* | 6/2009 | Ambrose ............ A61K 9/1647 424/426 |

OTHER PUBLICATIONS

Bruens, et al. "Porous Polymethylmethacrylate as Bone Substitute in the Craniofacial Area." Journal of Craniofacial Surgery, vol. 14, No. 1, Jan. 1, 2003.

Stevens, et al. "An articulated antibiotic spacer used for infected total knee adhoplasty: a comparative in vitro elution of Simplex and Palcaos bone cements." Journal of Orthopaedic Research, vol. 23, 2005, pp. 27-33.

Goodger, et al. "Methylmethacrylate as a space maintainer in mandibular reconstruction." J. Oral Maxillofacial Surgery, vol. 63, 2005, pp. 1048-1051.

* cited by examiner

COMBINED SPACE MAINTENANCE AND BONE REGENERATION SYSTEM FOR THE RECONSTRUCTION OF LARGE OSSEOUS DEFECTS

CROSS-REFERENCE TO RELATED APPLICATIONS

This application is a divisional application of U.S. patent application Ser. No. 13/548,385, filed Jul. 13, 2012, which is a continuation-in-part of International Application No. PCT/US2011/21266 filed Jan. 14, 2011 and claims priority to U.S. Provisional Patent Application Ser. No. 61/295,478, filed Jan. 15, 2010, both of which are incorporated herein by reference.

STATEMENT OF GOVERNMENT INTEREST

This invention was made with government support under Grant Number W81XWH-08-2-0032 awarded by the Department of Defense. The government has certain rights in the invention.

BACKGROUND

Traumatic bone injury is often accompanied by injury or loss of surrounding soft tissues. One of the major difficulties reconstructive surgeons face when treating injuries involving significant bone loss is contracture and scarring of the overlying soft tissue envelope, which may compromise facial projection and/or make staged repair of bony structures difficult. Definitive bone reconstruction is often delayed until soft tissue coverage and a sterile wound environment are achieved. Despite reports of local complications and wound infection rates as high as 100% for patients suffering gunshot wounds to the face, early definitive repair of facial gunshot wounds via free tissue transfer has become more common, as the well vascularized tissues that are transferred survive well in hostile wound environments.

The field of regenerative medicine and the technologies borne from tissue engineering offer great hope towards providing an alternative and possibly better approach to regenerating injured or destroyed tissues. Most proposed tissue engineering strategies, however, currently require planning in the form of material fabrication, autologous cell harvest and expansion, and/or ex vivo tissue generation. Additionally, little to no evaluation of tissue engineering approaches is currently performed in wound environments involving infection, significant vascular injury, and large-scale tissue devitalization such as that encountered in traumatic wounds.

In the absence of immediate reconstruction, clinical management of facial bone loss can involve the placement of an alloplastic space maintainer to provide a template for future definitive reconstruction and prevent wound contracture into the space normally occupied by bone. Solid polymethylmethacrylate (PMMA), is commonly used in such space maintenance applications. Although solid PMMA has many desirable characteristics for such applications (moldable, FDA-regulated, familiar to surgeons), a number of problems exist with respect to wound healing around solid PMMA implants and other alloplastic implants.

SUMMARY

The present disclosure provides, according to certain embodiments, systems, methods and compositions useful for treatment of traumatic bone injuries.

In one embodiment, the present disclosure provides a bone reconstruction system comprising: a space maintaining composition comprising porous polymethylmethacrylate; and an osseous generating construct comprising a polymethylmethacrylate chamber that comprises one or more osseous generating materials.

In another embodiment, the present disclosure provides a space maintaining composition comprising porous polymethylmethacrylate, wherein the porosity of the space maintaining composition is from about 10% to about 50%.

In another embodiment, the present disclosure provides a method comprising: placing a space maintaining composition comprising porous polymethylmethacrylate within an osseous defect; and placing an osseous generating construct comprising polymethylmethacrylate proximate to the osseous defect so as to generate an osseous construct.

In yet another embodiment, the present disclosure provides a method of making a space maintaining composition comprising: combining a methylmethacrylate monomer phase and an aqueous porogen phase comprising a hydrogel porogen; and forming a porous polymethylmethacrylate.

The features and advantages of the present invention will be apparent to those skilled in the art. While numerous changes may be made by those skilled in the art, such changes are within the spirit of the invention.

DRAWINGS

Some specific example embodiments of the disclosure may be understood by referring, in part, to the following description and the accompanying drawings.

FIG. 1 is a graph depicting porosity values as calculated by μCT. Samples were scanned and the resultant scans were reconstructed, reoriented, and binarized. Implant porosity was determined using a cylindrical (9 mm diameter×5 mm height) volume of interest slightly smaller than the implant dimensions to eliminate edge effects. Data are reported as means±standard deviation (n=3). The * over a bar denotes a statistically significant difference ($p<0.05$) as detected using ANOVA and Tukey's post hoc tests between the group marked and the group with the same % CMC but lower aqueous phase in relation to polymer phase.

FIG. 2 is graph depicting implant interconnectivity percentages as a function of the minimum interconnection size. Samples were scanned and processed as reported, and a built in software package was used to determine the percentage of the implant porosity that was accessible from outside the volume of interest. Data are reported as means±standard deviation (n=3).

FIG. 3 are representative images of implant cross sections and surfaces. Cylindrical implants (10 mm diameter×6 mm height) from each experimental group were scanned by μCT or SEM. Virtual μCT cross sections of the implants were made by slicing through the center of the axially oriented implant. For electron micrographs, the scale bar represents 500 μm.

FIG. 4 are representative gross views of harvested tissue covering the alveolus and implant. (A) Failure of wound healing over a solid PMMA implant is shown. The exposed implant is denoted by white arrows. (B, C) Well healed soft tissue covering the intraoral exposure is seen where dentition was removed to create a soft tissue defect over low porosity (B) and high porosity (C) implants.

FIG. 5 are representative light micrographs (25× magnification) of coronally sectioned tissue samples through the center of the A) Solid PMMA, (B) Low porosity, (C) High porosity space maintainers. The intraoral exposure of the solid implant (A) is shown with black arrows. Blue arrows denote the titanium plate used to stabilize the mandible. Tissue ingrowth into surface pores is seen within both porous implants, and, for all implants, the original defect space appears well maintained with minimal tissue collapse or contracture. In B and C, soft tissue discontinuities at the left (buccal) side of the implant capsule are due to embedding and processing artifacts. Scale bars represent 1 mm.

FIG. 6 are representative light micrographs (200× magnification) of the lingual surface of coronally sectioned tissue samples through the center of the implanted A) Solid PMMA, (B) Low porosity, (C) High porosity space maintainers. Regenerated bone is seen near the surface of all implants. A well-formed capsule is seen in (A), while only a thin layer of loosely organized fibrous capsule is seen at the surface of the low porosity space maintainer (B). An abundance of plasma cells is seen at the surface and penetrating the surface porosity of the highly porous space maintainer (C). Scale bars represent 100 µm for the larger images; the inset scale bar represents 25 µm.

FIG. 7 is a graph depicting score distributions for the graded (A) implant interface for all formulations tested in vivo and (B) tissue response within pores for the two porous implant formulations. Statistically significant differences ($p<0.05$) between groups, denoted by *, were determined using pairwise Dwass-Steel-Critchlow-Fligner tests for the implant interface scoring (A) and a Mann-Whitney U test for the tissue response within pores (B).

FIG. 8 is a graph depicting the cumulative release of colistin from PLGA microspheres. The inset pictures show the external (left) and internal (right) morphologies of PLGA microspheres characterized by SEM, where a smooth external surface and porous internal structure of the microspheres are observed. Error bars represent standard deviation for n=3. Size bars are 100 µm.

FIG. 9 are images representing surface morphologies of PLGA microsphere-incorporating porous constructs characterized by A) microCT (size bars represent 2 mm); B) SEM (lower magnification, size bars represent 500 µm); and C) SEM (higher magnification, size bars represent 100 µm).

Figure 12A:
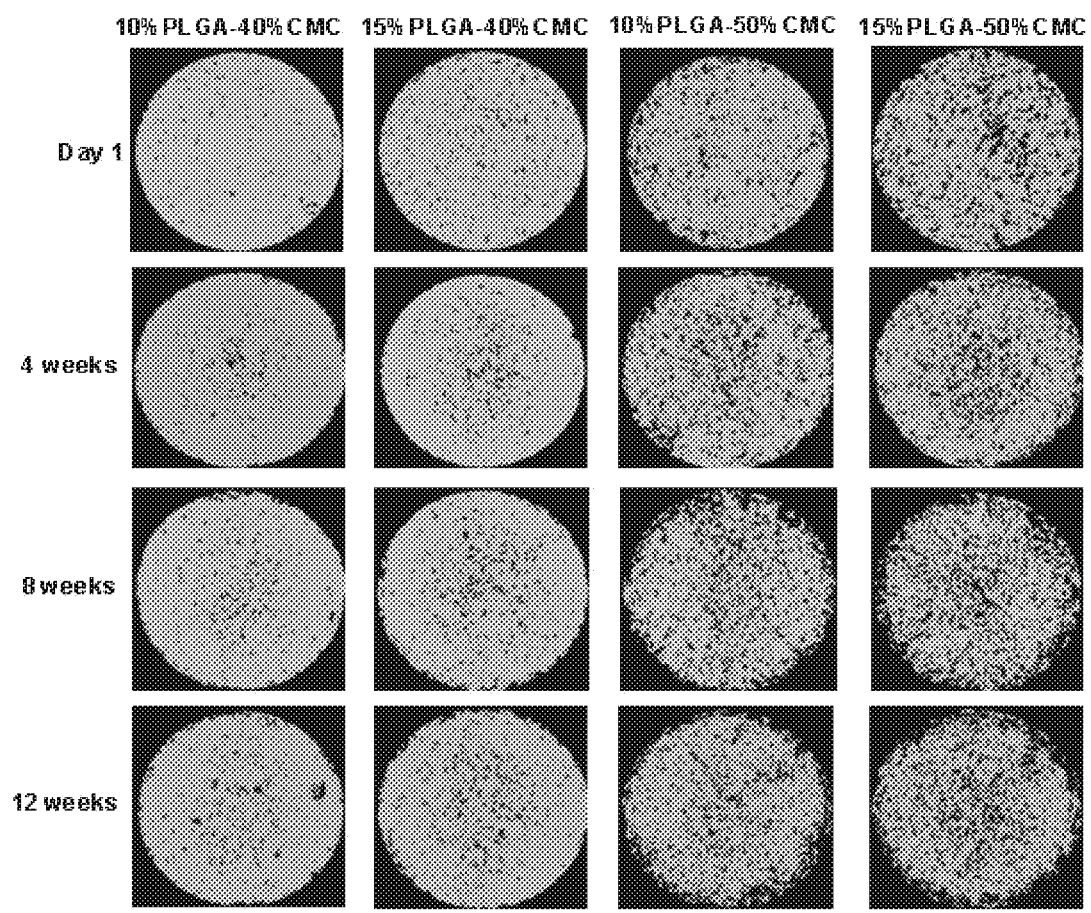
Figure 12B:
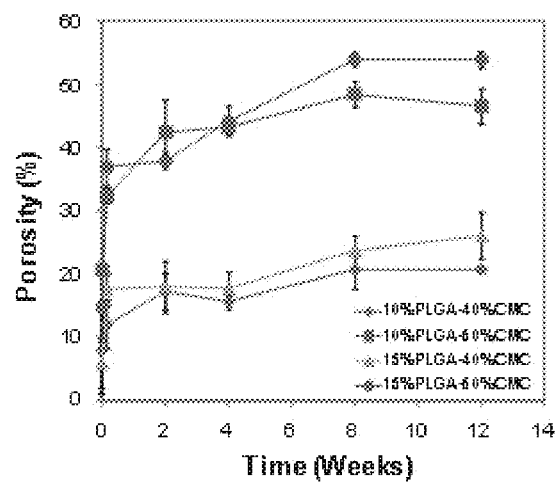
Figure 12C:
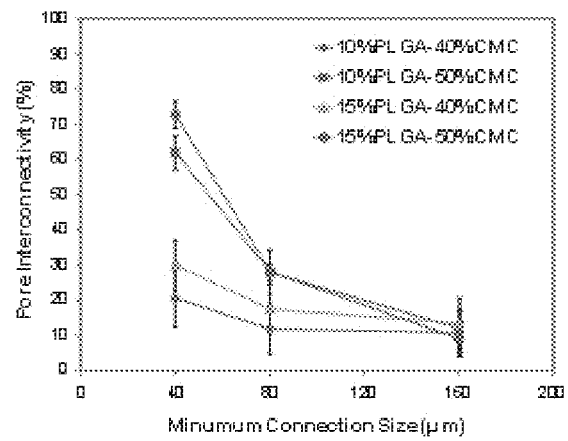

FIGS. 12A, 12B, and 12C depict degradation of PMMA/CMC/PLGA constructs characterized by microCT. FIG. 12A provides representative 3D reconstruction of cross-sections in the middle of cylindrical constructs (80 µm thickness, top view, size bar represents 2 mm) which illustrates increased pores and interconnectivity among pores due to CMC/PLGA component dissolution from the constructs. FIG. 12B provides that change of bulk porosity of constructs demonstrated an increased porosity over time. Higher CMC incorporation resulted in greater porosity initially and throughout the degradation process. FIG. 12C provides that pore interconnectivity of constructs after one day of degradation was significantly enhanced for the 50 wt % CMC-incorporating construct compared to that of the 40 wt % CMC-incorporating construct at smaller minimum connection sizes. Error bars represent standard deviation for n=3.

Figure 13:
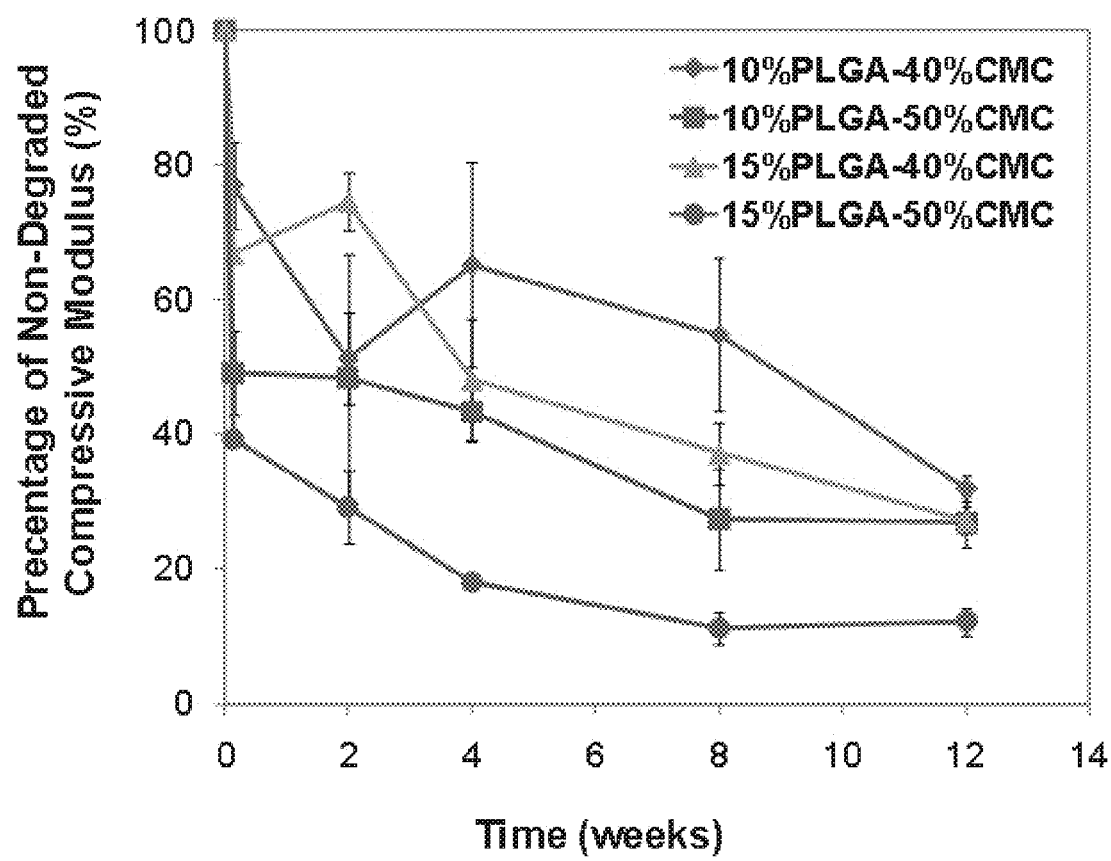

FIG. 13 is a graph depicting the change of compressive modulus of constructs during the degradation process, described as a percent of the compressive modulus of the degraded construct over that of the non-degraded construct: the decline of compressive mechanical properties of the cylindrical constructs (10 mm in diameter, 6 mm in height), whose dimension was designed for a mandibular defect model in rabbits, provided predictive insight into the expected mechanical performance of the construct over time in vivo. Error bars represent standard deviation for n=3.

Figure 14A:
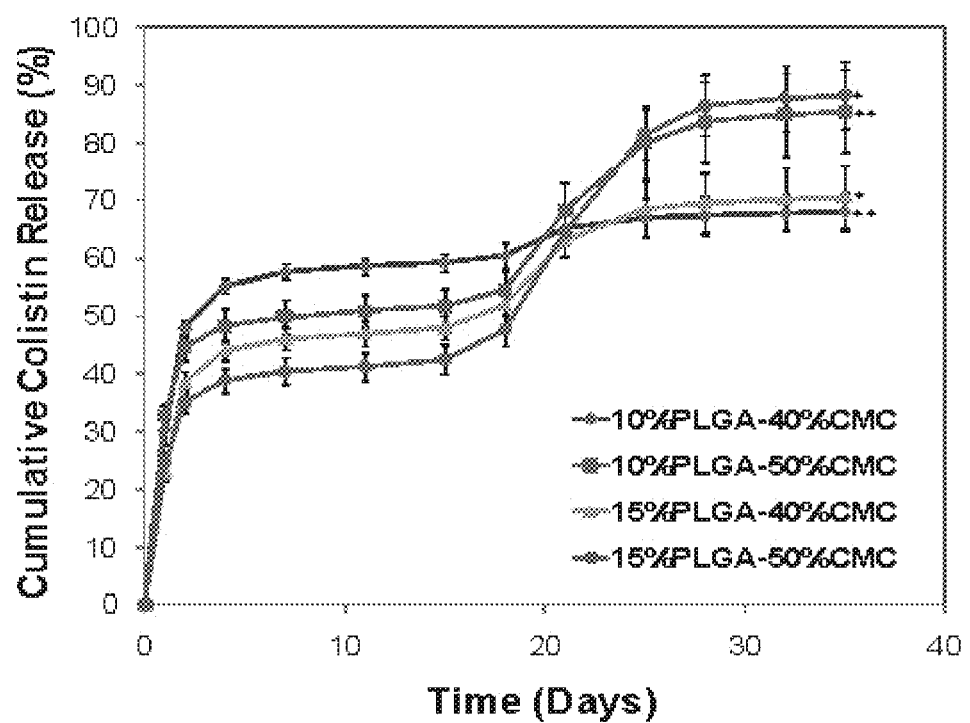
Figure 14B:
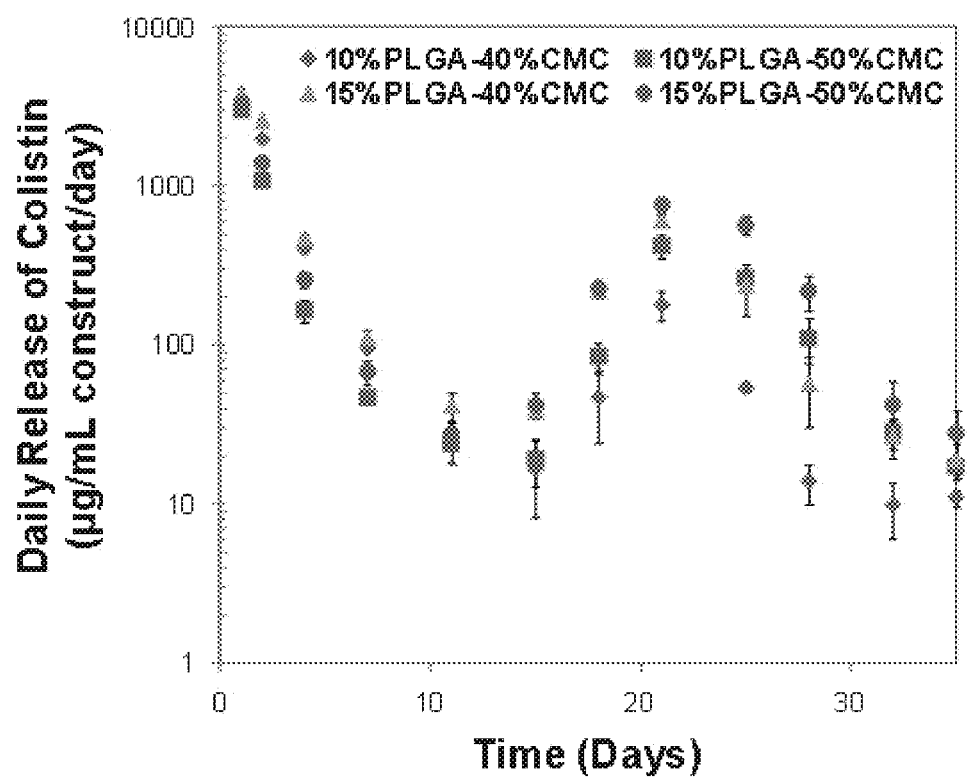

FIGS. 14A and 14B are graphs depicting in vitro colistin release from PMMA/CMC/PLGA constructs. FIG. 14A provides that the cumulative colistin release from PLGA/PMMA/CMC constructs presented a continuous colistin release over a period of 5 weeks. The total released colistin varied between 68.1±3.3-88.3±5.8% depending on the composition of the construct. Statistical significance between relevant groups is denoted by * and ** ($p<0.05$). FIG. 14B provides that the daily release of colistin, described as the concentration of released colistin divided by the corresponding release time in days, demonstrated that a constantly high colistin concentration (well above the reported MIC of colistin against its susceptible species) was created via controlled colistin release over 5 weeks. Error bars represent standard deviation for n=3.

Figure 15:
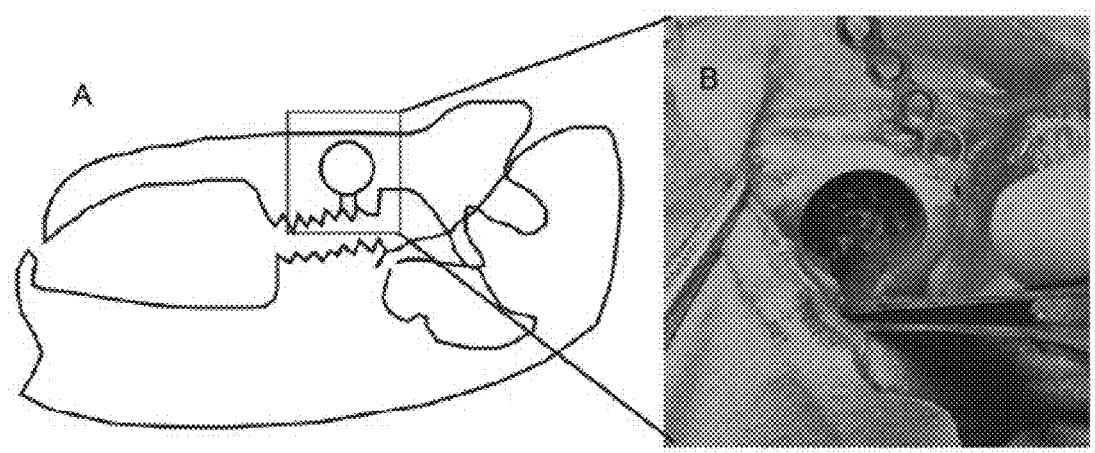

FIG. 15 depict the rabbit mandibular defect model in the supine position showing (A) skeletal location and (B) operative photograph.

Figure 16:
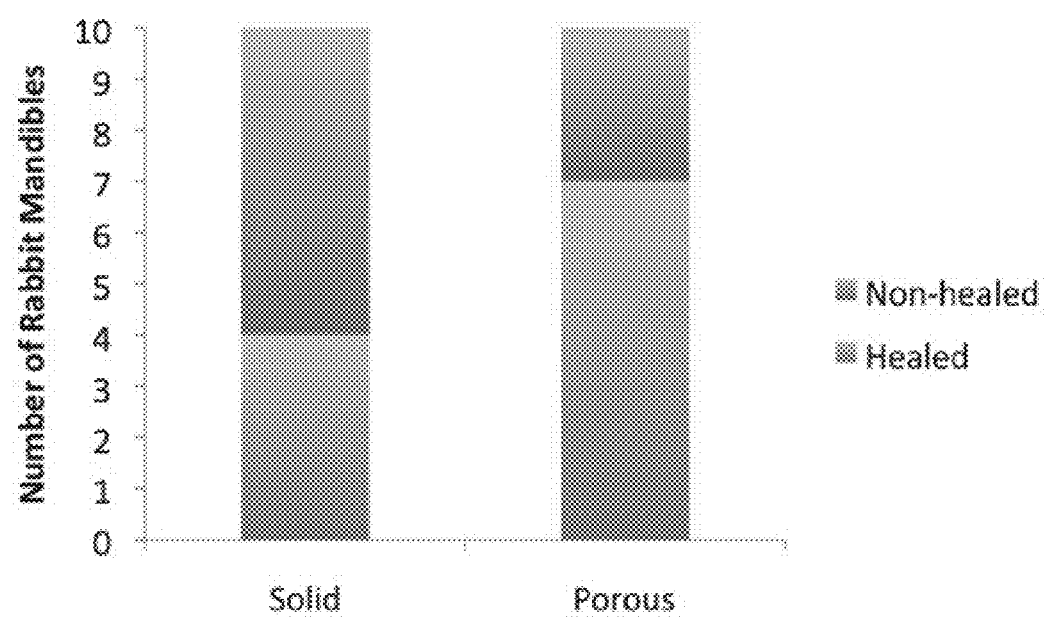

FIG. 16 is a graph depicting the gross evaluation results of oral mucosal healing of solid and porous implants (16.9% theoretical porosity) created intraoperatively.

Figure 17A:
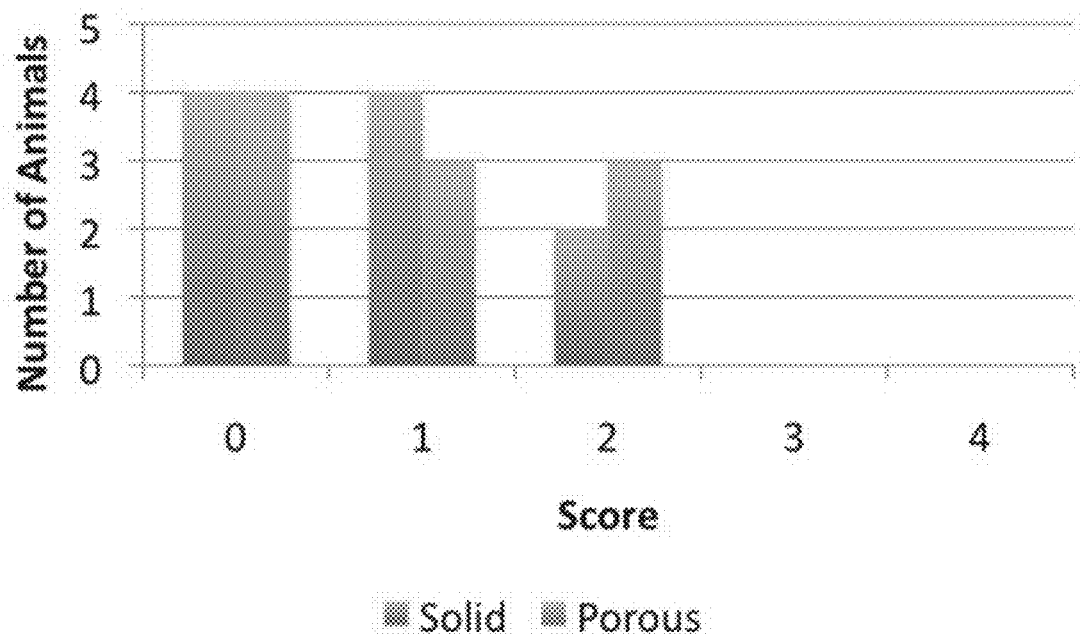
Figure 17B:
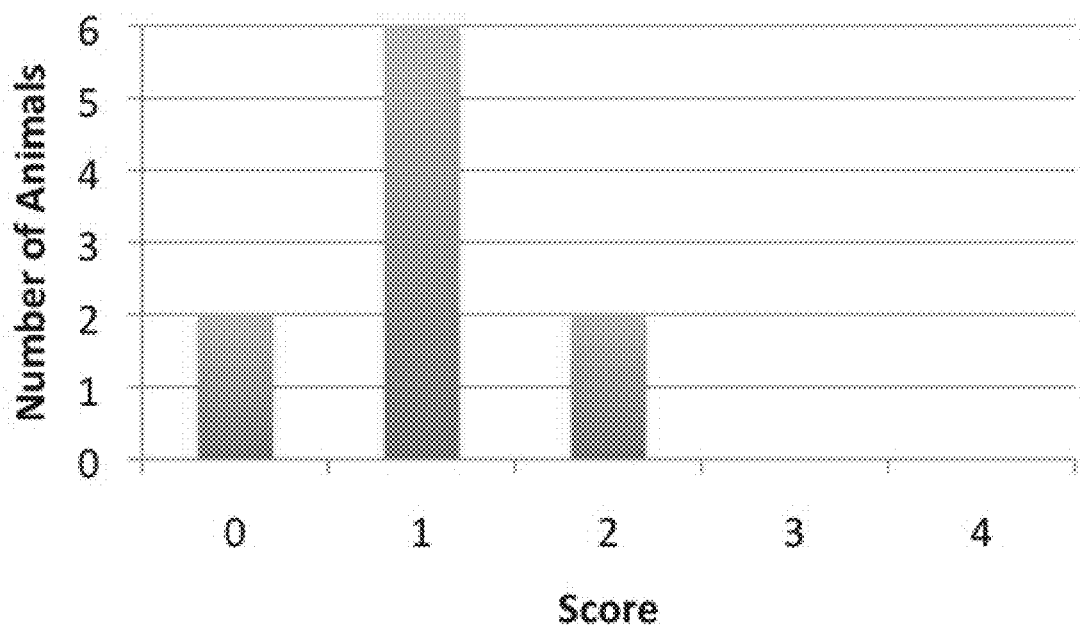

FIGS. 17A and 17B are graphs depicting histologic scores of the tissue (FIG. 17A) at the tissue-implant interface and (FIG. 17B) in the pores of the implants created intraoperatively.

Figure 18:
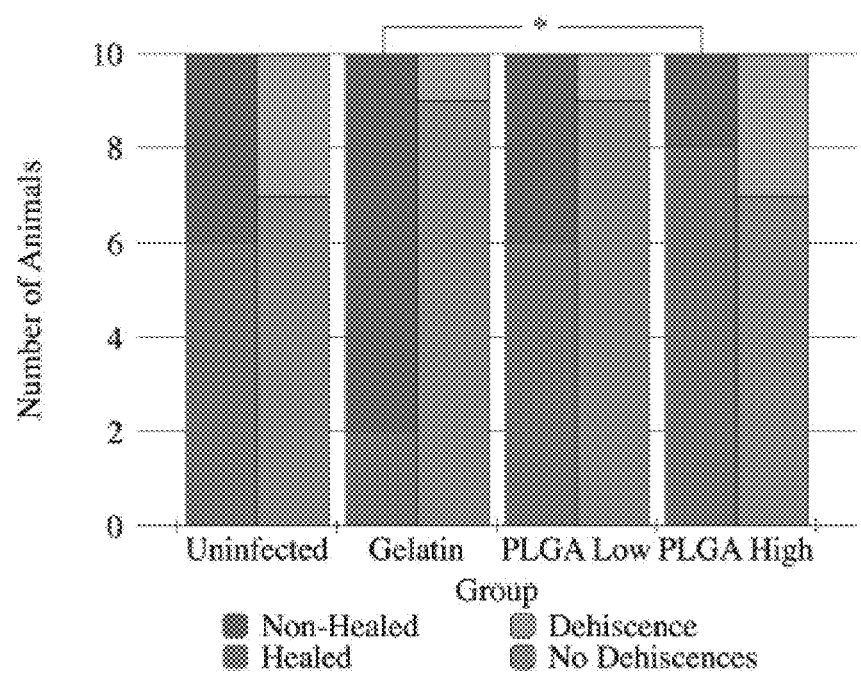

FIG. 18 is a graph showing number of specimens with well-healed (blue) vs. non-healed (red) oral mucosa and number of specimens with a dehiscence (orange) and those without (green). * indicates significance ($p<0.05$).

Figure 19:
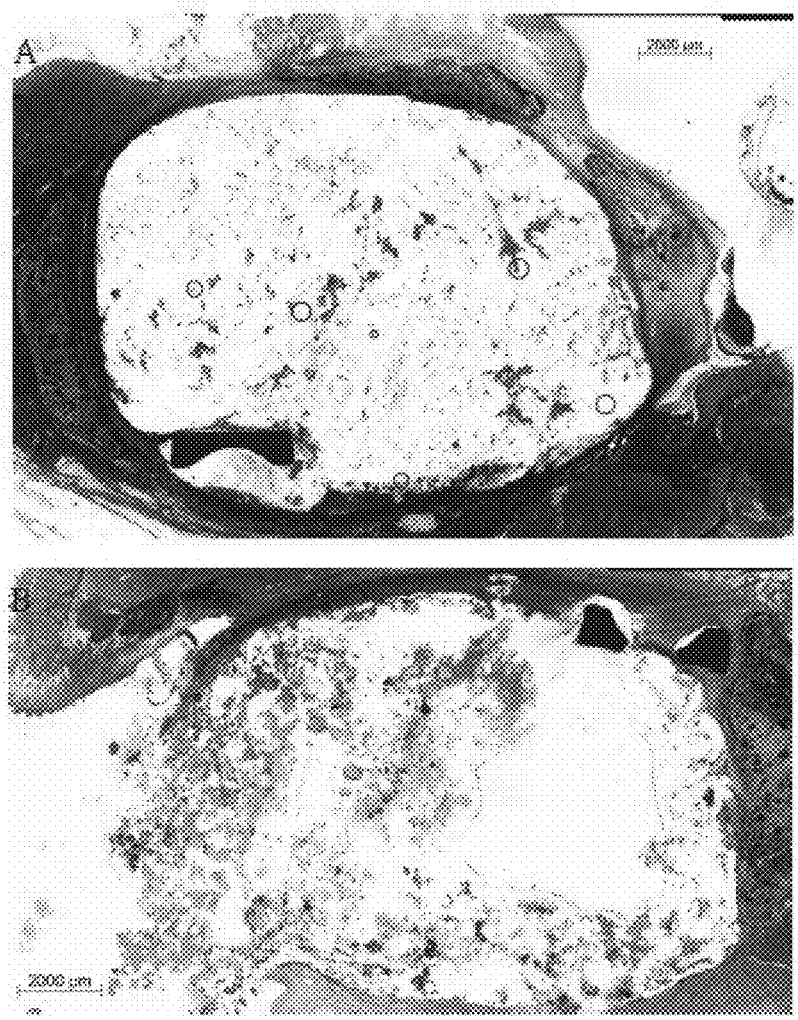

FIG. 19 are representative histological images showing (A) well-healed and (B) non-healed oral mucosa.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure provides, according to certain embodiments, systems, methods and compositions useful for treatment of traumatic bone injuries. According to certain embodiments, the present disclosure provides systems, methods and compositions that may be used for space maintenance in areas where significant volumes of bone have been lost, as well as for simultaneous treatment of wound infections or release of bioactive factors to aid in wound healing and tissue regeneration. The systems, methods and compositions of the present disclosure may be used as a part of a staged approach for regenerating large bone and soft tissue defects, such as those encountered due to traumatic injury or large scale tissue resection.

In one embodiment, the present disclosure provides a system comprising a space maintaining composition comprising porous polymethylmethacrylate; and an osseous generating construct comprising a polymethylmethacrylate chamber that comprises one or more osseous generating materials. According to certain embodiments, a space maintaining composition may be placed within an osseous defect and the osseous generating construct may be placed proximate to the osseous defect, e.g., placed against the cambial side of the periosteum of an existing, intact bone, so as to generate an osseous construct. The osseous generating construct can be filled with a number of osseous generating materials known in the art to aid in the formation of bone tissue. In one embodiment, the osseous generating construct may be filled with morselized autologous bone as described in Miller M. J., Goldberg D. P., Yasko A. W., Lemon J. C., Satterfield W. C., Wake M. C., Mikos A. G. Guided bone growth in sheep: A model for tissue-engineered bone flaps. Tissue Eng. 2, 51, 1996. In other embodiments, the osseous generating materials may comprise a demineralized bone matrix, or an engineered matrix consisting of a scaffold made of natural or synthetic polymer, ceramic or metal material, with or without autologous cells, and with or without drugs or factors such as recombinant human bone morphogenetic proteins. Over the course of the next weeks to months, bone will fill the osseous generating construct while the bony defect space is maintained by the space maintaining composition. Once the desired amount of bone has filled the osseous generating construct, the construct may be removed with or without an adjacent blood supply such that a prefabricated bone graft or bone flap is now available to be used for bone repair. The space maintaining composition can then be removed and definitive reconstruction with the generated bone graft or flap can then be performed.

For the purposes of facilitating a long-term tissue engineering approach to treating osseous defects, a space maintaining composition of the present disclosure may allow time for a regenerative medicine approach to be used to definitively regenerate the injured or absent tissue. In addition to providing space maintenance, a space maintaining composition of the present disclosure may be used to "prime" the defect site, enabling better success of the definitive regenerated tissue construct.

In general, the space maintaining compositions of the present disclosure may be capable of not only maintaining the osseous void and prevent soft tissue collapse or contracture into the space, but also may allow or promote soft tissue coverage and healing without serving as a nidus for local infections. In certain embodiments, the present disclosure provides space maintaining compositions with reproducibly tunable pore structure fabricated using a hydrogel as an aqueous porogen. Such space maintaining compositions feature a porous structure to promote wound/tissue healing over the material and implant retention at the host site.

Porosity, pore structure, and interconnectivity, in certain embodiments of the space maintaining compositions of the present disclosure, may impart selective properties concerning cellular ingrowth and/or drug or bioactive factor release. Surface pores of a sufficient size may allow soft tissue adherence and integration with the material surface, while interconnection sizes of a smaller size may prevent deeper ingrowth, but allow for release of certain drugs or bioactive factors from deeper pores through the interconnections. Accordingly, in certain embodiments, the present disclosure provides space maintenance compositions with surface pores having a diameter of from about 50 µm to about 150 µm. In other embodiments, the space maintenance compositions may have interconnectivities less than about 60% for connection sizes of 50 µm or larger.

In one embodiment, the space maintaining compositions of the present disclosure may comprise porous polymethylmethacrylate. In some embodiments, the porosity of the space maintaining composition may be in a range of from about 10% to about 50%. In some embodiments, the porosity of the space maintaining composition may be in a range of from about 10% to about 30%. It should be noted that, in some embodiments, it may be desirable for soft tissue integration onto the surface only for the space maintaining composition to comprise a higher degree of closed pores (e.g., pores which are not interconnected) so as to promote tissue adhesion and surface integration. In some embodiments, the porous polymethylmethacrylate may include sufficient open pores to facilitate release of bioactive molecules and/or drugs, with the remainder, or substantially all of the remainder, comprised of closed pores. For example, while the porosity of the space maintaining composition may be in a range of from about 10% to about 50%, the majority may comprise closed pores. In some embodiments, the porosity of the polymethylmethacrylate is displayed with a bias proximate to the surface of the composition. In this way, the pores provide a structural feature capable of facilitating tissue adhesion and surface integration.

In some embodiments, the present disclosure also provides methods for forming a space maintaining composition of the present disclosure. Accordingly, in one embodiment, a methylmethacrylate monomer phase is combined with an aqueous porogen phase comprising a hydrogel porogen to form a porous polymethylmethacrylate. This composition may be prefabricated or created intraoperatively by placing in a mold or molding by hand, respectively, until hardened due to polymerization of methyl methacrylate. In certain embodiments, varying the amount of hydrogel porogen within the aqueous phase and the relative amount of aqueous phase to monomer/polymer phase may allow for well-controlled porosity and pore interconnectivity. In general, higher percentages of porogen result in greater porosity within the space maintaining composition, while increasing the viscosity of the aqueous phase porogen by incorporating greater amounts of the porogen within the hydrogel may lead to a more consistent pore size and higher pore interconnectivity when the minimum interconnection size was decreased. In some embodiments, the aqueous porogen phase may be present in an amount of about 10 weight percent to about 50 weight percent. In some embodiments, the hydrogel porogen is present in the aqueous porogen phase in an amount of about 7 weight percent to about 9 weight percent. Examples of suitable hydrogel porogens may include, but are not limited to, carboxymethylcellulose (CMC), gelatin, collagen, pluronic, hyaluronic acid, alginate, chitosan, fibrin, agarose, poly(acrylic acid), poly(vinyl alcohol), poly(vinyl phosphonic acid), poly(glutamic acid), poly(ethylene glycol), poly(ethylene oxide), poly(phosphazene), oligo(poly(ethylene glycol) fumarate), poly(N-isopropyl acrylamide), and poly(hydroxyethyl methacrylate).

In certain embodiments, a delivery system is incorporated into a space maintaining composition of the present disclosure to provide delivery of an agent. The agent may be an antibiotic, bioactive factor, and the like. For example, in certain embodiments, an antibiotic delivery system is incorporated into the space maintaining composition to treat and/or prevent local infections, potentially eliminating the infection-related complication associated with space maintenance. Infections following traumatic injuries are a common occurrence. Latent or active posttraumatic and post-surgical infections may potentially hinder wound healing and tissue regeneration, underscoring the importance of effective, early eradication/prevention by antibiotic drugs. Such a delivery system, in general, may comprise biodegradable polymer microparticles or nanoparticles, such as polyanhydrides, polyesters, polyphosphazenes, polyamides, polyurethanes, polyacetals, polyortho esters, and poly(alpha-hydroxy esters) (e.g., poly(lactic-co-glycolic acid) (PLGA)). In this system, the drug or factor may be loaded, coated, entrapped or grafted to/in the polymer particle. This approach, among other things, minimizes the need for potentially toxic high serum concentrations of antibiotic over extended periods. In other embodiments, the delivery system may be used for the controlled release of bioactive factors such as growth factors (e.g., bone morphogenetic protein 2 and vascular endothelial growth factor).

In some embodiments, the present disclosure provides a regenerative medicine approach comprising a first stage using temporary space maintenance to not only maintain the void space, but also to prime the wound site for later definitive reconstruction. The initial space maintenance using a space maintaining composition preserves the original dimensions of the bony defects and prevents soft tissue ingrowth while, importantly, allowing for successful wound/tissue healing over the material. Successful space maintenance creates a soft tissue envelope with definitely preserved volume and well-healed surrounding tissues, ideal for the placement of an implant designed for bone regeneration (e.g., a vascularized bone flap or tissue engineered bone graft conforming to the preserved dimensions of the defect) during the subsequent reconstruction stage.

To facilitate a better understanding of the present invention, the following examples of certain aspects of some embodiments are given. In no way should the following examples be read to limit, or define, the entire scope of the invention.

EXAMPLE 1

Materials and Methods

Experimental Design

In the first part of this example, porous PMMA implants were synthesized and characterized using a CMC hydrogel as an aqueous phase to impart porosity on the implants. The percent of CMC in the aqueous phase and the ratio of aqueous phase:polymer phase were varied in order to control the bulk and surface characteristics. Following characterization of the porous implants, two formulations, one with high bulk porosity and pore interconnectivity and one with lower porosity and less pore interconnectivity, were compared over 12 weeks in vivo to a solid PMMA implant within a modified rabbit mandibular defect.

Implant Fabrication and Characterization

Solid and porous PMMA implants were fabricated using a clinical grade PMMA bone cement (SmartSet High Viscosity, DePuy Orthopaedics, Warsaw, Ind.) consisting of a powder of methylmethacrylate/methyl acrylate copolymer, benzoyl peroxide, and zirconium dioxide and a liquid phase with methylmethacrylate (MMA), N,N-dimethyl-p-toluidine, and hydroquinone. For the solid implants, the solid and powder phases were mixed according the manufacturer's specifications for approximately 90 seconds and, once they reached a dough-like consistency, packed into custom-fabricated 10 mm diameter×6 mm height cylindrical Teflon® (DuPont, Wilmington, Del.) molds. The solid implants were then allowed to harden at room temperature for 30 minutes before being removed from the molds and vacuum-dried overnight.

For porous implants, 7 wt % and 9 wt % CMC hydrogels were prepared by dissolving the appropriate amount of United States Pharmacopeia grade low viscosity CMC (Spectrum Chemical Manufacturing Corp., Gardena, Calif.) in distilled water. The powder component of the PMMA cement was then mixed with the CMC hydrogel such that the powder was uniformly suspended within the aqueous phase. The liquid component of the PMMA cement was then added to the mixture of aqueous/powder phases. Aqueous phase weight percentages of 30, 40, and 50 wt % were used to fabricate the implants, resulting in 6 experimental groups. The aqueous and polymer phases were then stirred by hand for approximately 90 seconds and packed into Teflon® molds of the same size as the solid PMMA implants. The porous implants within molds were then allowed to harden for 30 minutes before being removed from the molds, placed within individual cassettes, and the aqueous phase was then leached from the implants in deionized, distilled water as previously described in Patel Z. S., Young S., Tabata Y., Jansen J. A., Wong M., Mikos A. G. Dual delivery of an angiogenic and an osteogenic growth factor for bone regeneration in a critical size defect model. Bone. 43, 931, 2008. The porous PMMA implants were then vacuum dried overnight in a laboratory freeze dryer (Lyph-Lock 4.5, Labconco Corp., Kansas City, Mo.).

Implant porosity and pore interconnectivity were analyzed using microcomputed tomography (µCT) as previously described in Young S., Patel Z. S., Kretlow J. D., Murphy M. B., Mountziaris P. M., Baggett L. S., Ueda H., Tabata Y., Jansen J. A., Wong M., Mikos A. G. Dose effect of dual delivery of vascular endothelial growth factor and bone morphogenetic protein-2 on bone regeneration in a rat critical-size defect model. Tissue Eng Part A. 15, 2347, 2009. Briefly, implants (n=3) from all experimental groups were scanned using a SkyScan 1172 µCT imaging system (SkyScan, Aartselaar, Belgium). High resolution 1280×1024 pixel images were created by scanning at an 8 µm/pixel resolution with no filter at voltage and current settings of 40 kV and 250 µA, respectively. Serial tomograms were reconstructed, resliced, and analyzed using NRecon and CTAn software packages provided by SkyScan. For porosity and pore interconnectivity analyses, the scanned object volumes were binarized using a global threshold of 60-255. Porosity and interconnectivity were determined using a 9 mm diameter×5 mm height cylindrical volume of interest to eliminate edge effects. Pore interconnectivity was determined by repeatedly applying a shrink wrap algorithm with minimum interconnection sizes ranging from 40-320 µm. Interconnectivity is reported as the percentage of pore volume accessible from outside the volume of interest with pores considered accessible only if the interconnection to that pore allowed a sphere with diameter of the user defined minimum interconnection size to pass through.

Scanning electron microscopy (SEM) was also used to examine the external surface of the implants. Implant surfaces were sputter-coated with gold for 40 s at 100 mA using a CrC-150 sputtering system (Torr International, New Windsor, N.Y.) and observed at an accelerating voltage of 10 kV using a FEI Quanta 400 field emission scanning electron microscope (FEI company, Hillsboro, Oreg.).

In Vivo Implant Evaluation

Solid PMMA implants and porous implants (9 wt % CMC within the aqueous phase and both 30 and 40 wt % total aqueous phase in the implant) were evaluated in vivo using a modification of a nonhealing rabbit mandibular defect model as described in Young S., Bashoura A. G., Borden T., Baggett L. S., Jansen J. A., Wong M., Mikos A. G. Development and characterization of a rabbit alveolar bone non-healing defect model. J Biomed Mater Res A. 86, 182, 2008. All surgical procedures followed protocols approved by the Institutional Animal Care and Use Committees at both Rice University and the University of Texas Health Science Center at Houston. Eighteen healthy male adult New Zealand White rabbits (n=6 per group), at least 6 months old and weighing 3.5-4 kg were purchased from Myrtle's Rabbitry (Thompson Station, Tenn.). Prior to implantation, all implants were sterilized using ethylene oxide.

Briefly, each animal was given preoperative intramuscular doses of buprenorphine hydrochloride (0.1 mg/kg body weight) for postoperative analgesia and 0.5 mL Durapen® (150,000 U/mL penicillin G benzathine and 150,000 U/mL penicillin G procaine) for perioperative antibiotic coverage. Prior to induction, ketamine hydrochloride (40 mg/kg body weight) and xylazine hydrochloride (7.5 mg/kg body weight) were given, after which rabbits were placed in a supine position, intubated and placed under general anesthesia using an isoflurane/O2 mixture (2.5-3% isoflurane for induction, 2% for maintenance) with constant cardiac and respiratory monitoring. The animals were then surgically prepped and draped, after which a 7 cm midline incision through the skin and superficial fascia was made beginning 0.5 cm posterior to the mentum. Using blunt dissection and electrocauterization, the left masseter was exposed and the soft tissue along the inferior border of the body of the left hemimandible was mobilized such that the periosteum covering the body of the mandible could be incised and elevated, exposing a 4 cm×1.5 cm area on the lateral surface of the mandible. A 10 mm titanium trephine (Ace Surgical Supply, Inc., Brockton, Mass.) attached to a Stryker TPS® surgical handpiece (Stryker, Kalamazoo, Mich.) operating at 15,000 rpm with copious normal saline irrigation was used to create a bicortical defect through the exposed body of the left mandible. A 701 bur in combination with the surgical drilling unit was used to cut a 2-3 mm window through the alveolar ridge in the middle of the defect to provide access for removal of the crowns of the associated teeth and provide intraoral exposure of the defect. The defect site was thoroughly washed with normal saline, after which an implant was placed within the defect. The order of implant placement was randomized; and none of the surgical personnel, who were the same throughout the study, were aware of which implant was being used. Prior to closure, a titanium supporting plate (1.5 mm 6-hole heavy gauge titanium; Synthes, West Chester, Pa.) was secured in place to prevent iatrogenic fracture during the course of the study. The incision was then closed in 3 layers (muscle, fascia, and skin) using degradable sutures (Vicryl polyglactin sutures, Ethicon, Somerville, N.J.). Following wound closure, anesthesia was reversed, and the animals were extubated.

Postoperatively, the animals were given access to food and water ad libitum. Food was limited to a soft recovery diet (Critical Care for Herbivores, Oxbow Pet Products, Murdock, Nebr.) and shredded or mashed fruits and vegetables to reduce stress on the mandible. All animals survived the 12-week post-operative period without complications.

Gross Characterization

After 12 postoperative weeks, each rabbit was euthanized via intravenous injection of 1 mL Beuthanasia-D® (390 mg/mL pentobarbital sodium and 50 mg/mL phenytoin sodium). The left hemimandibles were then carefully dissected from the cranium with care taken to preserve the soft tissue surrounding the implant and within the oral cavity. The oral mucosa and dentition covering the alveolus of each specimen was examined to detect any areas of implant or bone exposure. Specimens were individually placed in 10% neutral buffered formalin and stored on a shaker table at 4° C. for 72 h.

Histology

After fixation, samples were dehydrated and stored in 70% of ethanol and then embedded in MMA. Following polymerization of the MMA, 3 coronally oriented 10 μM thick sections through the center of each implant were cut using a modified diamond saw technique as described in van der Lubbe H. B., Klein C. P., de Groot K. A simple method for preparing thin (10 microm) histological sections of undecalcified plastic embedded bone with implants. Stain Technol. 63, 171, 1988, and subsequently stained using methylene blue/basic fuchsin.

Each of the stained sections was analyzed using light microscopy (Zeiss Axio Imager Z1 and AxioCam MRc 5, Carl Zeiss AG, Oberkochen, Germany) by two blinded observers (SY and FKK). A quantitative scoring system (Table 1) was used to score the tissue response at the implant interface and within the pores of the porous implants.

TABLE 1

| Description | Score |
| --- | --- |
| Hard tissue response at scaffold-bone interface | |
| Direct bone to implant contact without soft interlayer | 4 |
| Remodeling lacuna with osteoblasts and/or osteoclasts at surface | 3 |
| Majority of implant is surrounded by fibrous tissue capsule | 2 |
| Unorganized fibrous tissue (majority of tissue is not arranged as capsule) | 1 |
| Inflammation marked by an abundance of inflammatory cells and poorly organized tissue | 0 |
| Hard tissue response within the pores of the scaffold | |
| Tissue in pores is mostly bone | 4 |
| Tissue in pores consists of some bone within mature, dense fibrous tissue and/or a few inflammatory response elements | 3 |
| Tissue in pores is mostly immature fibrous tissue (with or without bone) with blood vessels and young fibroblasts invading the space with few macrophages present | 2 |
| Tissue in pores consists mostly of inflammatory cells and connective tissue components in between (with or without bone) OR the majority of the pores are empty or filled with fluid | 1 |
| Tissue in pores is dense and exclusively of inflammatory type (no bone present) | 0 |

Statistical Analyses

Implant porosity data were analyzed using single factor analyses of variance (ANOVA) with post hoc pairwise comparisons made using Tukey's HSD. Oral mucosal wound healing, as observed grossly and confirmed by microscopy, was analyzed using a Fisher-Freeman-Halton test. Histological scoring was analyzed using nonparametric statistics. The tissue response at the implant interface was analyzed using a Kruskal-Wallis one-way analysis of variance with subsequent pairwise analyses made using the Dwass-Steel-Critchlow-Fligner test. A Mann-Whitney U test was used to analyze the tissue response within the pores of the two porous implant types. The a priori level of significance for all analyses was chosen as $\alpha=0.05$. All analyses were performed using R version 2.10.0 (R Foundation for Statistical Computing, Vienna, Austria).

Results

Implant Fabrication and Characterization

Figure 1:
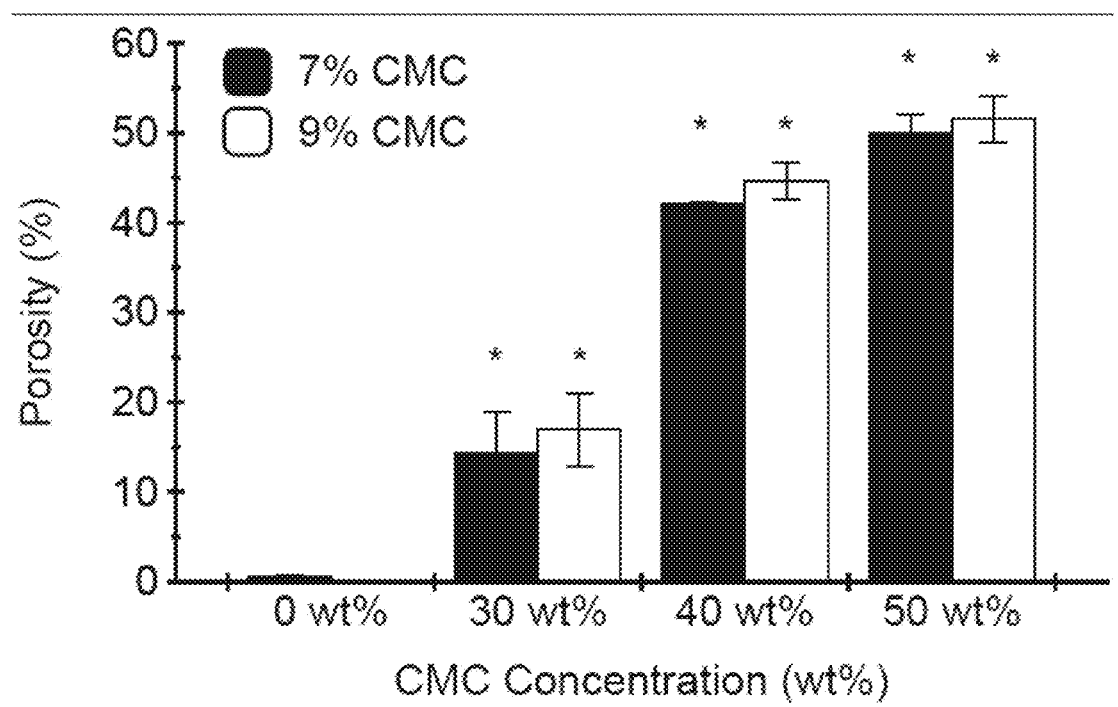

Porous PMMA/CMC implants were reproducibly fabricated as described in the Materials and Methods section. MicroCT analyses showed that porosity increased as expected with increasing incorporation of the aqueous phase (FIG. 1). Significant differences in implant porosity were observed between all groups as the aqueous phase incorporation increased. Varying the amount of CMC within the aqueous phase did not significantly alter the implant porosity.

Figure 2:
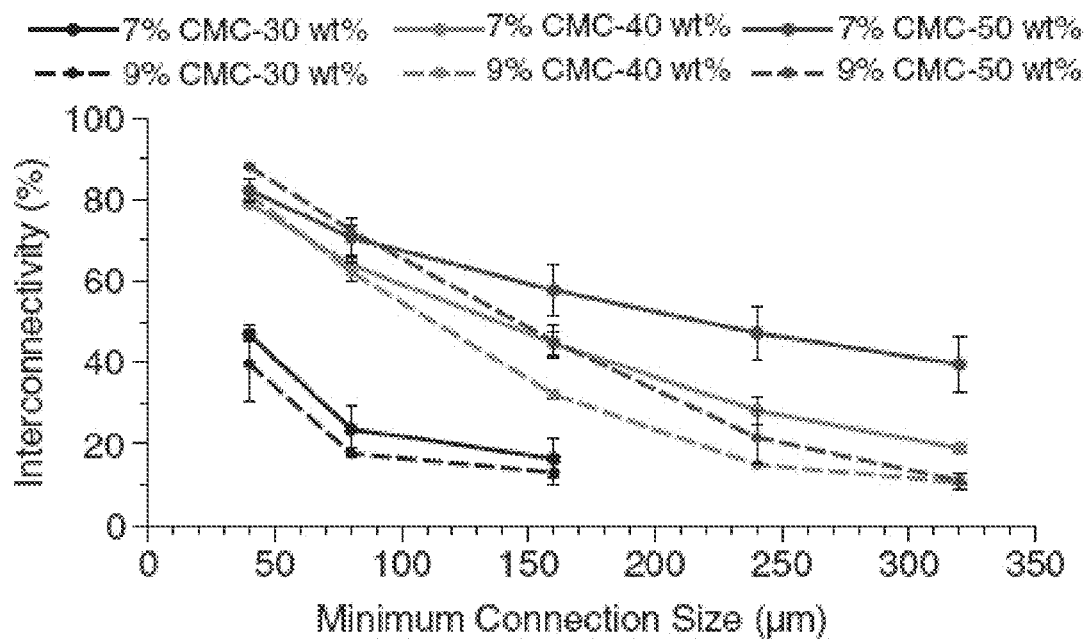

Pore interconnectivity also increased with increasing aqueous phase incorporation (FIG. 2). Interconnectivity appeared to be affected by the percentage of CMC in the aqueous phase; the more negative slope observed for implants with 9% CMC within the aqueous phase indicates that more of the interconnections in these implants were smaller than for those implants fabricated with 7% CMC in the aqueous phase.

Figure 3:
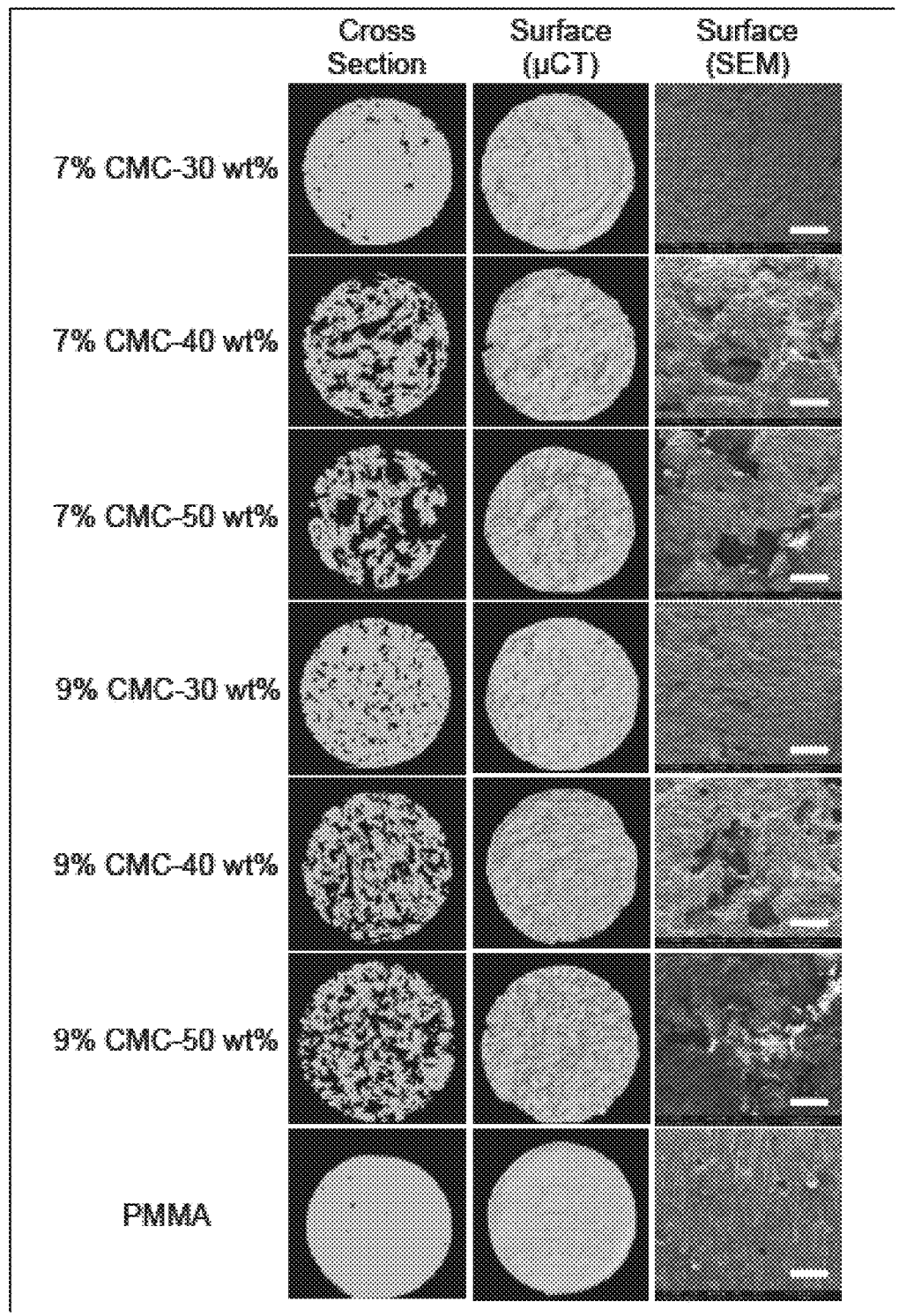

SEM images and µCT reconstructions also showed differences in the porosity and surfaces of the fabricated implants (FIG. 3). The porosity increases with increasing aqueous phase incorporation quantitatively detected with µCT are seen in cross sections and surface images of the implants. Furthermore, the pore size appears more consistent within implants fabricated using 9% CMC in the aqueous phase, likely resulting in the relative abundance of smaller pore interconnections within these implants when compared to those fabricated using 7% CMC.

In Vivo Implant Evaluation

Based on the implant characterization, solid PMMA implants, 9% CMC 30 wt % (16.9±4.1% porosity, 39.7±9.4% interconnectivity at a 40 µm minimum connection size) and 9% CMC 40 wt % (44.6±2.1% porosity, 81.2±1.0% interconnectivity at a 40 µm minimum connection size) implants were chosen for implantation in the in vivo phase of the study. All animals survived the surgery and post-operative period without complications. No changes in eating habits or activity were noted by the investigators, husbandry staff, or veterinary staff.

Gross Characterization

Figure 4:
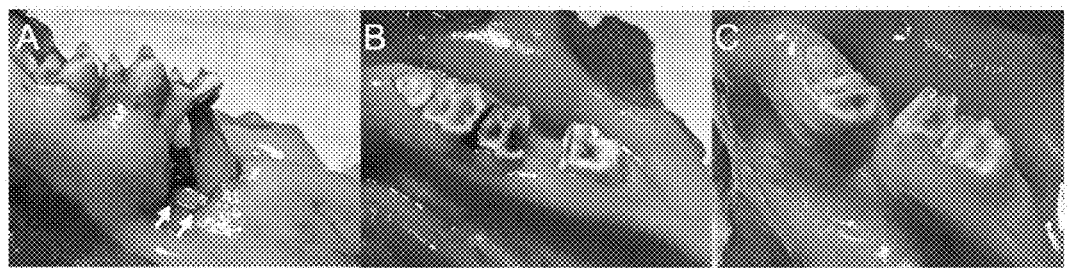

At the time of animal euthanasia and implant/hemimandible harvest, no signs of mobility or infection were noted in any of the animals or visible tissues following harvest. Wound healing (closure) of the oral mucosa over the alveolar ridge at the site of the intraoral communication was assessed grossly (FIG. 4) and correlated to histological results (Table 2) to confirm the gross observations.

TABLE 2

Oral Mucosal Coverage over Implant by Implant Type

| Implant type | Healed/Non-healed |
| --- | --- |
| Solid | 3/3 |
| Low porosity | 5/1 |
| High porosity | 5/1 |

Wound healing was considered incomplete when any exposed bone or implant could be grossly observed and histology also indicated a failure of soft tissue coverage over the implant or within the defect. The increase in oral mucosal wound healing observed in defects filled with both low and high porosity implants (83% of defects healed in each group) versus non-porous PMMA implants (50% healed) was not statistically significant (p>0.08).

Histology

Figure 5:
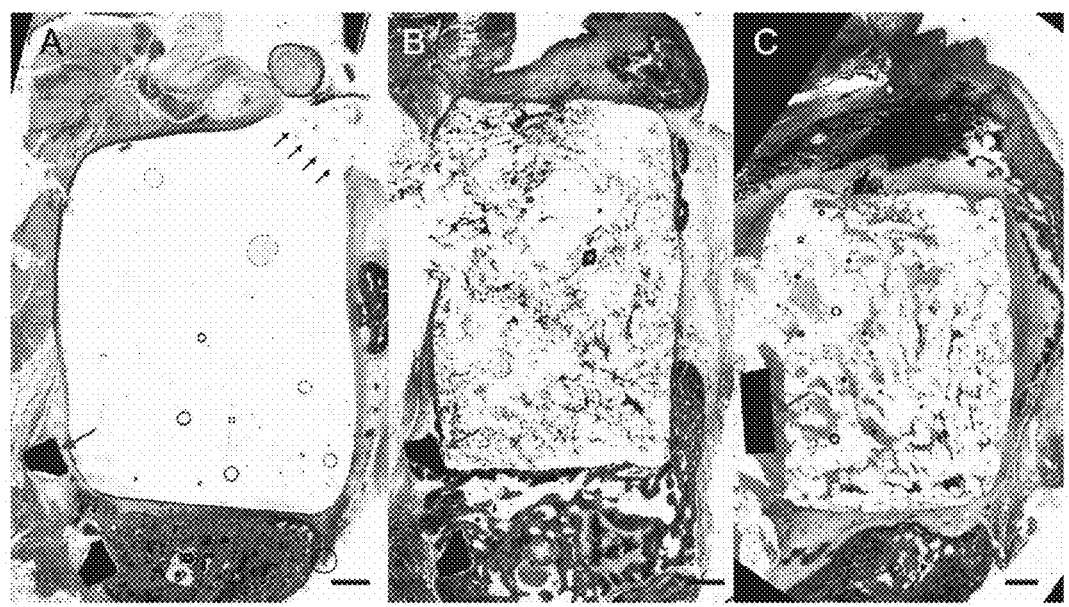

Histology and histological scoring were performed to assess the ability of the implants to maintain space within the surgically created osseous void and to view and quantify the soft tissue response around and within the implants. At low magnifications allowing coronal views of the entire implant and defect in cross section, all implants successfully maintained the defect space within the hemimandible. This space maintenance was confirmed by the lack of tissue collapse or contracture into the space occupied by the implants with the exception of tissue invading the pores of the porous implants (FIG. 5).

Figure 6:
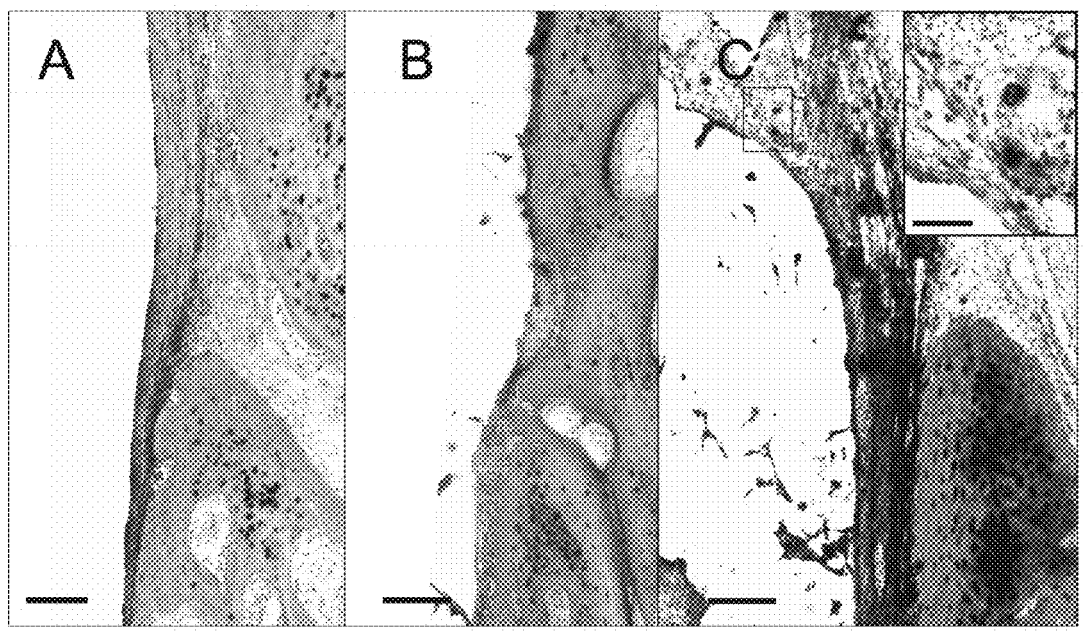
Figure 7:
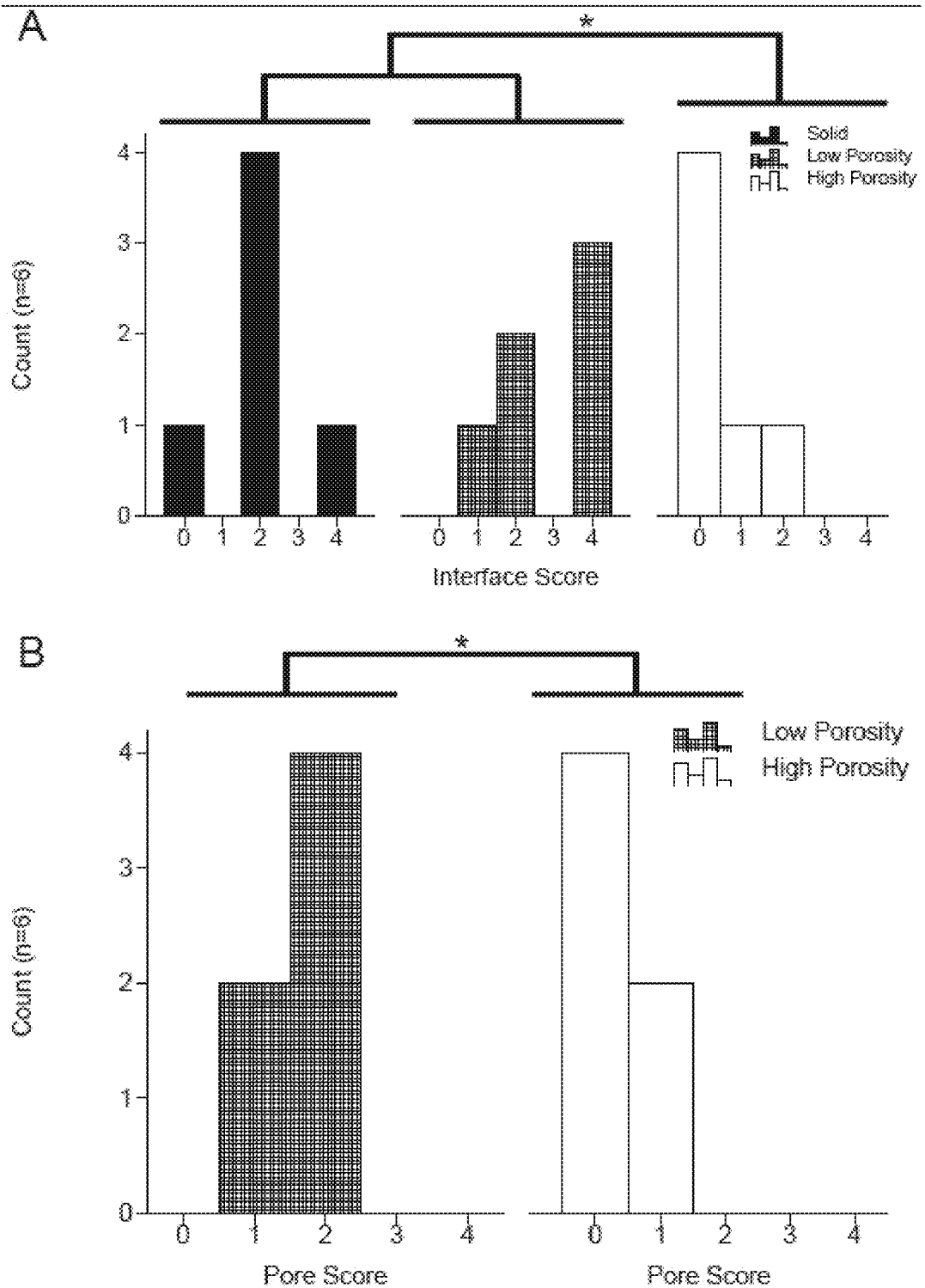

At higher magnification, the tissue response at the implant-tissue interface and within the implant pores could be observed (FIG. 6). At the implant-tissue interface, both the low porosity and solid implants were in many cases surrounded by a thin, well-organized fibrous capsule. The low porosity implants were also in direct contact in many areas with any newly formed bone observed at the implant interface. The high porosity implants were primarily surrounded by an abundance of inflammatory plasma cells at the implant interface, and a similar inflammatory cell population was observed within the pores of the highly porous implants. When a quantitative scoring system was applied, the interfacial tissue response for the highly porous implants was statistically significantly different from the response observed around both the solid and low porosity implants (FIG. 7, $p<0.05$). Similarly, the difference in tissue response within the pores of the low and high porosity implants was statistically significant (FIG. 7, $p<0.05$).

Discussion

Temporary space maintainers have historically been used clinically to prevent soft tissue collapse into bony defects and provide a template for delayed bone healing or grafting. Recently, however, space maintenance has been used infrequently, particularly in the staged repair of traumatic injuries, as immediate free tissue transfer has eliminated the need for space maintenance and staged repair. Additionally, problems with existing biomaterials such as problems with healing of surrounding tissues, implant extrusion, or bacterial colonization have further limited the use of space maintainers, particularly in applications where soft tissue healing or infection may be a concern. Unfortunately, due to limitations in current tissue engineering technology, injuries involving lacking or devitalized soft tissues or the possibility of infection are precisely the type a staged repair using temporary space maintenance might allow a regenerative medicine approach to be undertaken.

This example evaluated methods to reproducibly fabricate and characterize porous PMMA implants using a CMC porogen and to then test selected formulations in a non-healing bone defect in an animal model that approximated a more toxic wound environment than most traditional animal models. In the first part of this example, porous PMMA implants were fabricated in a one step process by incorporating a CMC hydrogel that could be leached away rapidly in vitro or in vivo. Varying both the amount of CMC within the aqueous phase and the relative amount of aqueous phase to polymer phase allowed for well-controlled porosity and pore interconnectivity. As expected, higher percentages of porogen resulted in greater implant porosity, while increasing the viscosity of the aqueous phase porogen by incorporating of greater amounts of CMC within the hydrogel led to a more consistent pore size and higher pore interconnectivity when the minimum interconnection size was decreased.

In the second part of this example, two formulations of porous PMMA implants and solid PMMA implants were implanted into non-healing rabbit mandibular defects that had been contaminated through an open communication with the oral cavity. Porous PMMA formulations were selected such that both a highly porous, highly interconnected implant (9% CMC 40 wt %) and an implant of lower porosity and lower interconnectivity could be compared (9%

CMC 30 wt %). Healing of the communication into the oral cavity was assessed as well as the tissue response both around and within the implants. All formulations successfully maintained space within the defect. Soft tissue was only observed within the defect when it was penetrating the pore network in the two formulations of porous implant. The oral mucosal defects created to allow communication into the bone defect healed in more cases (5/6 healed for both low and high porosity implants) when the bony defects were filled with porous implants than when filled with solid implants (3/6 healed), although the differences between groups was not statistically significant.

Although the gross mucosal defect closure over the high and low porosity implants was equivalent, microscopically, the tissue response around and within the pores of the low porosity implants was more favorable. At the implant—tissue interface, a small, well formed capsule or direct tissue—implant contact was typically observed around the low porosity implants. Immature fibrous tissue with few inflammatory elements was generally seen within the filled pores of the low porosity implants. Contrastingly, the tissue surrounding and within the pores of the highly porous implants was almost exclusively inflammatory, consisting mostly of plasma cells. Thus the low porosity and solid implants elicited a more favorable soft tissue response than the highly porous implants, while the porous implants may have provided a template for improved wound healing in comparison to the solid implants.

This example demonstrates one of the first systematic studies of fabrication methods to quantitatively examine the effect of both the ratio of aqueous phase to polymer phase and also the effect of the aqueous phase viscosity as done by varying the amount of CMC within the aqueous phase. Increasing the viscosity of the aqueous phase by using a 9 wt % CMC hydrogel, as opposed to a 7 wt % CMC gel, resulted in a more consistent pore architecture with smaller, more consistently sized pore interconnections. Because of this, both porous implant formulations chosen for the in vivo study were fabricated with 9 wt % CMC hydrogels. An additional benefit of the chosen materials is that both PMMA and CMC are FDA regulated for craniofacial applications, and the fabrication of the implants can be done in a standard operating room with only minor alterations in the manufacturer recommended preparation of PMMA.

A strength of the in vivo portion of this example was the development of a more clinically relevant animal model that may better simulate the type of clinical situation in which the technology investigated may be used. The animal model was based on a previously developed rabbit mandibular defect (Young S., Bashoura A. G., Borden T., Baggett L. S., Jansen J. A., Wong M., Mikos A. G. Development and characterization of a rabbit alveolar bone nonhealing defect model. J Biomed Mater Res A. 86, 182, 2008) that was modified to allow contamination of the wound through an opening into the oral cavity. This conferred several advantages. First, mucosal wound healing within the rabbit oral cavity is a well-established method for evaluating wound healing, particularly when evaluating biomaterial-guided wound healing. Second, in the clinical setting, the presence of intraoral communication is significantly correlated to decreased bone graft survival time, and thus an implant evaluation strategy that focuses on the closure of these communications is relevant for a situation where definitive repair will be performed using a standard or tissue engineered bone graft. With relation to the presence of these intraoral communications, infection is a major concern when dealing with any implantable biomaterial, particularly PMMA, and thus evaluating the tissue response to the implant in an environment where it will most likely be exposed to bacteria strengthens any conclusions drawn with respect to optimal material formulations. Finally, although the observed differences in oral mucosal wound healing does not allow one to draw any definitive conclusions about how the presence of porosity affected the oral mucosal wound healing, this example establishes the statistical parameters necessary to determine the statistical power needed to achieve significance in future studies using this model. While a difference in healing clearly existed between both the high and low porosity implants and the solid PMMA implants, the difference was not significant. Somewhat surprisingly, the difference in tissue response to the porous implants based on histological scoring was significantly different and may be an important parameter not only for initial wound healing but also for subsequent bone regeneration.

Using the methods described in this example for fabrication and evaluation, the porous PMMA implants appeared to promote or allow wound healing of the oral mucosa better than the solid implants. Significant differences in the tissue response to the two formulations of porous implants were also observed. A number of possible explanations exist for these two findings. The trend of improved wound healing with use of the porous implants may best be explained by increased tissue integration within the pores of the implants. This may have limited implant micromovement and improved the rate at which new tissue formed across the implant to close the communication. Similar improvements in wound healing and implant retention have been found when using porous polyethylene for the fixation of bone-anchored hearing aids.

The inflammatory tissue response around and within the highly porous implants was likely caused by increased bacterial seeding of these implants. The increased porosity and interconnectivity of these implants compared to those of the low porosity and lower interconnectivity group likely led to bacterial accumulation deeper within the implant in areas where the bacteria could not effectively be cleared. Kiechel et al. compared infection control within porous and nonporous PMMA seeded with *Staphylococcus aureus* and implanted in the paravertebral fascia of rabbits and found increased infections occurred in animals implanted with porous PMMA implants. Kiechel S. F., Rodeheaver G. T., Klawitter J. J., Edgerton M. T., Edlich R. F. The role of implant porosity on the development of infection. Surg Gynecol Obstet. 144, 58, 1977. Sclafani et al. found that increased porosity increased the resistance to infection in implants inoculated 14 days after implantation but not if the implants were inoculated at the time of implantation. Sclafani A. P., Thomas J. R., Cox A. J., Cooper M. H. Clinical and histologic response of subcutaneous expanded polytetrafluoroethylene (gore-tex) and porous high-density polyethylene (medpor) implants to acute and early infection. Arch Otolaryngol Head Neck Surg. 123, 328, 1997. Thus in applications and models where contamination or infection exists at the time of implant placement, an appropriate balance with respect to porosity is needed to allow tissue adhesion and implant integration but not bacterial seeding deep within the implant. If contamination is not present at the time of implantation, fibrovascular ingrowth into surface pores has been shown to occur rapidly and thus a more porous implant may be acceptable. Additionally, studies of induced membranes or capsules around PMMA implants suggest that the formation of well-formed capsule around the implants, as seen more frequently around the low porosity implants in this study, may facilitate greater success of later efforts aimed at definitive bone regeneration, provided the capsule is not destroyed during implant removal and any necessary debridement. Finally, it is important to note that the method of fabrication of the porous PMMA implants may lead to particulate PMMA release, which could account for the inflammatory response elicited by the highly porous implants.

EXAMPLE 2

The aim of the present example was to elucidate the influence of material composition of PMMA/CMC/PLGA constructs on their physical properties and provide insight into the expected space maintenance and drug delivery capability of the space maintainer over time in vivo. It was hypothesized that the overall porosity would be tailored by the incorporation of CMC hydrogel and would not be significantly changed with the addition of PLGA microspheres. The incorporation of PLGA microspheres in porous PMMA constructs was hypothesized to allow for a sustained, high concentration colistin release over weeks. To test these hypotheses, four formulations of PMMA/CMC/PLGA constructs with 40-50 wt % CMC and 10-15 wt % PLGA microsphere incorporation were investigated for surface and bulk morphology, porosity, pore interconnectivity and compressive mechanical properties initially and throughout a degradation process of 12 weeks. In vitro drug release kinetics were also examined over a period of 5 weeks.

Materials and Methods

Materials

Poly(lactic-co-glycolic acid) (PLGA) (copolymer ratio of 50:50, weight average molecular weight of 61.1 kDa and number average molecular weight of 37.3 kDa as determined by gel permeation chromatography based on polystyrene standards) was purchased from Lakeshore Biomaterials (Birmingham, Ala.). Colistin sulfate salt was purchased from Sigma-Aldrich (St. Louis, Mo.). PMMA cement (SmartSet, High Viscosity) was from DePuy Orthopaedics Inc. (Warsaw, Ind.). Carboxymethylcellulose sodium was purchased from Spectrum® chemical MFG Corp. (Gardena, Calif.). Poly(vinyl alcohol) (PVA) (88% hydrolyzed, nominal molecular weight 22 kDa) was from Acros Organics (Geel, Belgium). All other reagents were purchased from Sigma-Aldrich (St. Louis, Mo.) and used as received.

Preparation of Colistin-Loaded PLGA Microspheres

Colistin-loaded PLGA microspheres were fabricated by a water-in-oil-in-water (W/O/W) double emulsion solvent evaporation technique. Freitas S, Merkle H P, Gander B. Microencapsulation by solvent extraction/evaporation: reviewing the state of the art of microsphere preparation process technology. J Control Release 2005; 102:313-332. Briefly, PLGA polymer (2.0 g) was dissolved in methylene chloride at a concentration of 50 mg/mL as an oil phase, and colistin (650 mg) was dissolved in 2 mL distilled water (internal aqueous phase) containing 0.4 wt % PVA. The colistin solution was dispersed in the polymer solution by a homogenizer (PRO250, Pro Scientific Inc., Monroe, Conn.) at 26,000 rpm for 30 s. This stable W/O emulsion was slowly added into an aqueous solution (external aqueous phase, 400 mL) containing 0.4 wt % PVA and 0.5 M NaCl under stirring at 500 rpm and the solution was stirred at 500 rpm for 30 min. Solvent removal and microsphere hardening was achieved by stirring at 300 rpm for another 3.5 h. The microspheres were isolated by centrifugation, washed with distilled water three times, and then vacuum-dried for 24 h.

The drug content in the PLGA microspheres was determined by first dissolving microspheres in methylene chloride and then extracting colistin with phosphate buffered saline (PBS) buffer (pH 7.4). Briefly, 20 mg colistin-loaded microspheres were dissolved in 1 mL methylene chloride and then 20 mL PBS was added to the solution. The solution mixture was vigorously stirred for 2 h allowing for the extraction of colistin by the aqueous phase and evaporation of the organic solution.

The colistin concentration in the PBS buffer was analyzed by high-performance liquid chromatography (HPLC) (Waters®, Milford, Mass.). The HPLC system consisted of a Waters 2695 separation module and a 2996 photodiode array (PDA) detector. The separation was performed using an XTerra® RP 18 column (250 cm×4.6 µm, Waters®) at a column temperature of 45° C. and a flow rate of 0.5 mL/min in a mobile phase consisting of acetonitrile (HPLC grade with 0.1 vol % trifluoroacetic acid) and water (HPLC grade with 0.1 vol % trifluoroacetic acid). Peaks were eluted with a linear gradient of 10-65% acetonitrile in water over 20 min. Absorbance was monitored at $\lambda=214$ nm. The two main components colistin A and colistin B were eluted at approximately 14.9 min and 15.7 min, respectively. Standard solutions with colistin in PBS buffer (pH 7.4) were tested in the range of 5-1000 µg/mL. Calibration curves were obtained using the combined peak areas of colistin A and colistin B versus the colistin concentration.

Preparation of Microsphere-Incorporating Porous PMMA Constructs

Antibiotic-releasing porous PMMA constructs were fabricated by mixing a clinical grade bone cement formulation of PMMA powder and MMA liquid with a CMC hydrogel and colistin-loaded PLGA microspheres. The percentage of PLGA microspheres was varied (10 wt % or 15 wt %) to adjust the drug content in each volume unit of the construct. The percentage of CMC hydrogel was varied (40 wt % or 50 wt %) to control the surface/bulk porosity of the constructs (Table 3).

TABLE 3

Composition of microsphere-incorporating PMMA/CMC/PLGA constructs prior to fabrication and in dried samples

| PMMA/CMC/PLGA constructs | Initial composition | | Composition of dried sample | | | Drug content |
| --- | --- | --- | --- | --- | --- | --- |
| | PLGA conc. (wt %) | CMC conc. (wt %) | PLGA conc. (wt %) | CMC conc. (wt %) | salt (wt %) | mg/mL scaffold |
| 10% PLGA-40% CMC | 10 | 40 | 9.4 | 5.7 | 1.5 | 11.2 |
| 15% PLGA-40% CMC | 15 | 40 | 14.1 | 5.7 | 2.3 | 16.6 |
| 10% PLGA-50% CMC | 10 | 50 | 9.2 | 8.3 | 1.5 | 9.1 |
| 15% PLGA-50% CMC | 15 | 50 | 13.8 | 8.3 | 2.2 | 13.4 |

The CMC hydrogel was prepared by dissolving carboxymethylcellulose sodium (9 wt %) in distilled water, which resulted in a highly viscous hydrogel. The following mixing procedure was employed to provide the most reproducible and homogeneous distribution of hydrogel phase according to previous experience: first the PMMA powder and the PLGA microspheres that were needed for 10 or 15 wt % relative to the polymer phase (PLGA+PMMA+MMA) were fully mixed using a spatula. Then the powder mixture was dispersed in a predetermined weight of CMC hydrogel (40 or 50 wt % in the constructs of CMC+PLGA+PMMA+MMA) by manual stirring. The monomer liquid was added into the mixture and the two phases were mixed carefully to ensure uniform distribution of the monomer while minimizing air entrapment. After the mixture reached a dough-like consistency (approximately 90 s), the mixture was subsequently inserted into Teflon molds. The cement mixtures were allowed to harden in the molds for 30 min at ambient temperature (21° C.). After the removal of constructs from the molds, the constructs were vacuum-dried overnight.

Cylinders 6 mm in diameter and 12 mm in height were used for mechanical testing based on the International Organization for Standardization Standard ISO5833. Cylinders 10 mm in diameter and 6 mm in height, which were designed for a previously developed rabbit mandibular defect model were used for the degradation study/in vitro drug release.

Scanning Electron Microscopy (SEM)

SEM was employed to examine the external and internal morphology of colistin-loaded PLGA microspheres and the surface roughness and porosity of microsphere-incorporating constructs. The microspheres or the surface of constructs were sputter-coated with gold for 40 s at 100 mA using a CrC-150 sputtering system (Torr International, New Windsor, N.Y.) and observed under a FEI Quanta 400 field emission scanning electron microscope (FEI company, Hillsboro, Oreg.) at an accelerating voltage of 10 kV.

Setting Temperature and Time

Setting temperature and time were measured simultaneously by recording the temperature of the cement mixture as a function of time after the addition of the last component. According to ISO5833 for acrylic resin cements, the dough-like mixture was packed into a Teflon cylindrical mold (60 mm in diameter, 6 mm in height) where a temperature measurement probe connected to a multimeter (Datalogging Multimeter, Data Acquisition System ML720, Extech Instruments Corp., MA) was positioned in the center of the mold to record the temperature of the mixture every 0.2 s until the temperature began to drop. The setting temperature was calculated as:

$$T_{set}=(T_{max}+T_{amb})/2$$

where $T_{max}$ is the highest temperature attained during polymerization, and $T_{amb}$ is the recorded ambient temperature.

For each measurement, the temperature change was plotted against time and the setting time $t_{set}$ was measured from the beginning of mixing until the temperature reached the setting temperature $T_{set}$. The average and standard deviation of $T_{set}$ and $t_{set}$ were determined from three measurements.

Microcomputed Tomography (microCT)

A SkyScan 1172 microCT imaging system (Aartselaar, Belgium) was used to perform nondestructive imaging and quantify the 3D microarchitectural morphology of original and degraded constructs. The samples (n=3) were imaged with an X-ray tube voltage of 40 kV and current of 250 mA without a filter. Volumetric reconstruction and analysis were conducted using the software NRecon and CTAn provided by SkyScan. The images obtained from acquisition were first reconstructed to serial coronal-oriented tomograms using a 3D cone beam reconstruction algorithm and then segmented into binary images using adaptive local thresholding to distinguish polymer material from pore space and to eliminate background noise. An optimal threshold value of 60-255 was applied for all 3D reconstructions and quantitative analyses. Representative 3D reconstructions of constructs were generated based on the binarized tomograms to visually show the 3D models of microstructures of scaffolds. To quantitatively analyze the porosity and interconnectivity, a cylindrical volume of interest (VOI) 5.8 mm in diameter and 9.8 mm in height was selected in order to eliminate potential edge effects. The bulk porosity of constructs was calculated as:

Bulk porosity=100%−vol % of binarized object in VOI

The interconnectivity was quantified as the fraction of the pore volume in a construct that was accessible from the outside through openings of a certain minimum size (a sphere diameter of 40-160 µm). A shrink-wrap process was performed to shrink the outside boundary of the VOI in a construct through any openings where the spheres could pass, and the total volume of the VOI (V) and the volume of the binarized object ($V_{shrink-wrap}$) were measured. If 100% of the porosity was accessible to the sphere, then $V=V_{shrink-wrap}$; otherwise, $V_{shrink-wrap}<V$ because the volume of the VOI includes the volume of the construct plus any void space that is not accessible. Interconnectivity was calculated as follows:

Interconnectivity=$(V-V_{shrink-wrap})/(V-V_m) \times 100\%$ where V is the total volume of the VOI, $V_{shrink-wrap}$ is the VOI volume after shrink-wrap processing, and $V_m$ is the volume of construct materials.

Compressive Modulus and Strength

The compressive mechanical properties of microsphere-incorporating constructs were measured to establish the influence of CMC/PLGA incorporation on mechanical performance. In accordance with ISO5833, 6 mm×12 mm cylindrical constructs (n=6) were compressed along their long axis at a cross-head speed of 20 mm/min using a mechanical testing machine (MTS, 858 Mini Bionix, Eden Prairie, Minn.) with a 10 kN load cell.

Constructs (cylinders of 10 mm in diameter, 6 mm in height) that were designed for a mandibular defect model were used in the degradation study. Although these dimensions do not conform to ISO specifications, the mechanical testing over time of these degraded constructs was performed to provide insight on the change of mechanical performance over time in vivo. The degraded cylindrical constructs (n=3) were compressed along their long axis at a cross-head speed of 1 mm/min with a 10 kN load cell (MTS).

For both compressive tests, force and displacement were recorded throughout the compression and converted to stress and strain based on the initial specimen dimensions. The compressive modulus was analyzed using the TestStar 790.90 mechanical data analysis package designed by MTS and calculated as the slope of the initial linear portion of the stress-strain curve. The offset compressive yield strength was determined as the stress at which the stress-strain curve intersected with a line drawn parallel to the slope defining the modulus, beginning at 2.0% strain (based on ISO5833).

In Vitro Drug Release

The in vitro drug release was carried out in triplicate at 37° C. in PBS buffer (pH 7.4). Each construct was incubated in 5 mL PBS buffer under mild shaking. At predetermined time intervals, the release medium from each sample was completely removed and replaced with fresh PBS buffer. The release medium was filtered with a 0.2 μm filter and tested by HPLC to determine the colistin concentration. The HPLC method is described above. The cumulative release (%) was expressed as the percent of total colistin released over time. The daily release of colistin was calculated from the absolute amount of colistin released between three or four consecutive days divided by the corresponding release time as well as the construct volume, and was expressed as μg colistin/mL construct/day.

Statistical Analysis

For porosity, setting temperature and time, and compressive modulus data, statistical analysis was performed with a single-factor analysis of variance (ANOVA) with a 95% confidence interval ($p<0.05$). In the case of statistically significant differences, Tukey's post hoc test was conducted. For comparing the cumulative release data in the in vitro colistin release study, a repeated measures analysis of variance was performed, followed by a Tukey's multiple comparison test to determine statistical significance at an alpha level of 0.05. The comparison of the first day release of constructs with PLGA microspheres and the pairwise comparison of the release rate of sustained release period (phase 3) of constructs were performed with a single-factor analysis of variance followed by a Tukey's multiple comparison test. Data are presented as means±standard deviation.

Results

Colistin-Loaded PLGA Microspheres

The ability of PLGA microspheres to control colistin release was first examined. Colistin-loaded PLGA microspheres with a 16.1±2.5 wt % drug loading were prepared by a water-in-oil-in-water double emulsion method. The SEM images of external and internal morphologies (FIG. 8 inset) showed spherically shaped microparticles with smooth surfaces and a highly porous internal polymeric matrix. The colistin-loaded PLGA microspheres exhibited a typical three-phase release profile (FIG. 8), including an initial burst of 52.3±6.2% release at days 0-2, a lag phase characterized by a moderate drug release (0.9±0.2% per day at days 2-11), and a sustained, accelerated drug release (1.9±0.2% per day at days 11-25) lasting for two weeks. The PLGA microspheres alone exhibited a continuous colistin release over a period of 4 weeks with an 87.5±9.9% total colistin release.

Microsphere-Incorporating PMMA/CMC/PLGA Constructs

Figure 9:
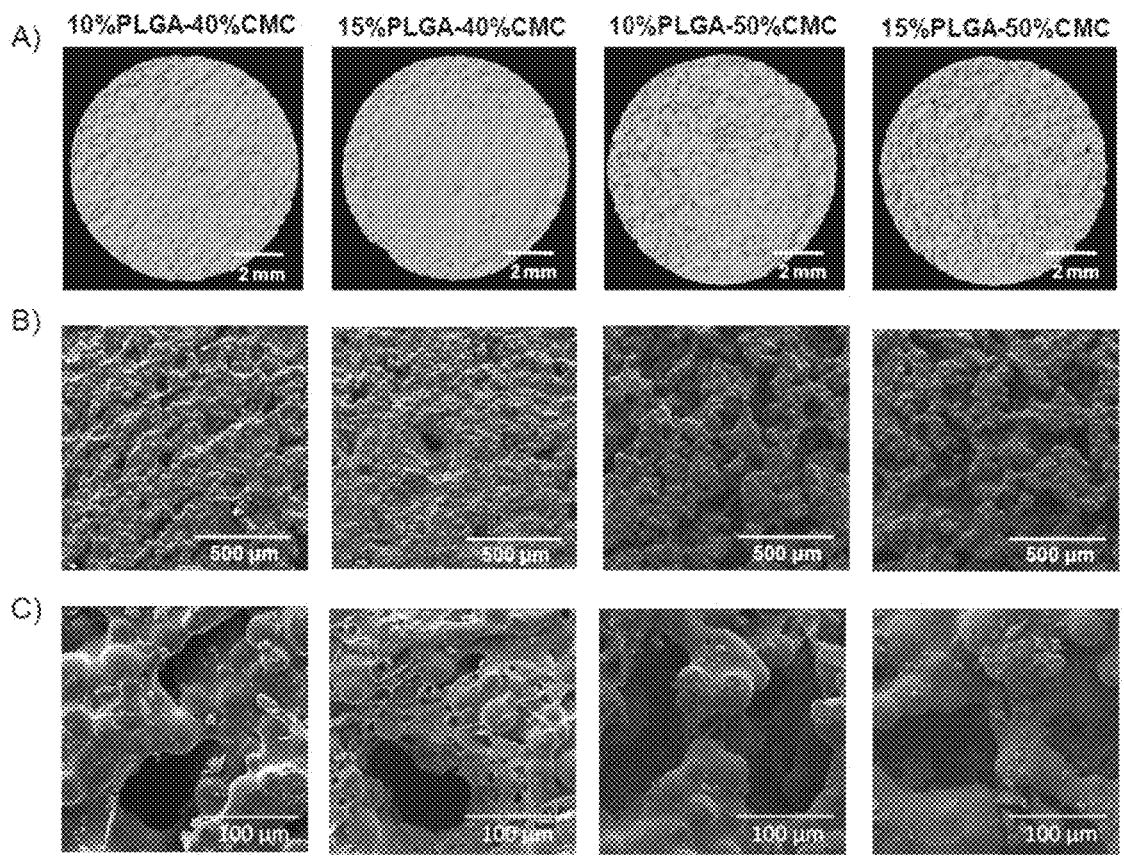

To prepare the microsphere-incorporating porous constructs, the PLGA microspheres were first mixed with the PMMA powder, and then the powder mixture was homogenously dispersed in the CMC hydrogel, followed by the addition of the MMA liquid phase. Curing of the mixture occurred when the initiator in the powder phase started polymerization of the reactive MMA monomer, thus trapping the PLGA microspheres, PMMA microparticles, and CMC hydrogel within the polymerizing matrix. The CMC hydrogel dispersed throughout the polymerizing matrix, yielding the initial surface/bulk porosity. The surface morphologies of dry construct samples were characterized by microCT and SEM (FIG. 9). Higher CMC hydrogel incorporation (50 wt % versus 40 wt %) resulted in greater roughness and pore depth on the construct surface (FIGS. 9A and 9B). Importantly, the PLGA microspheres were homogeneously dispersed among the PMMA microparticles (the PLGA microspheres could not be distinguished from the PMMA particles in SEM images due to similar sizes) (FIG. 9C). The PLGA microspheres and PMMA particles were more likely entrapped within the continuous polymer phase rather than localized inside the pores.

Figure 10:
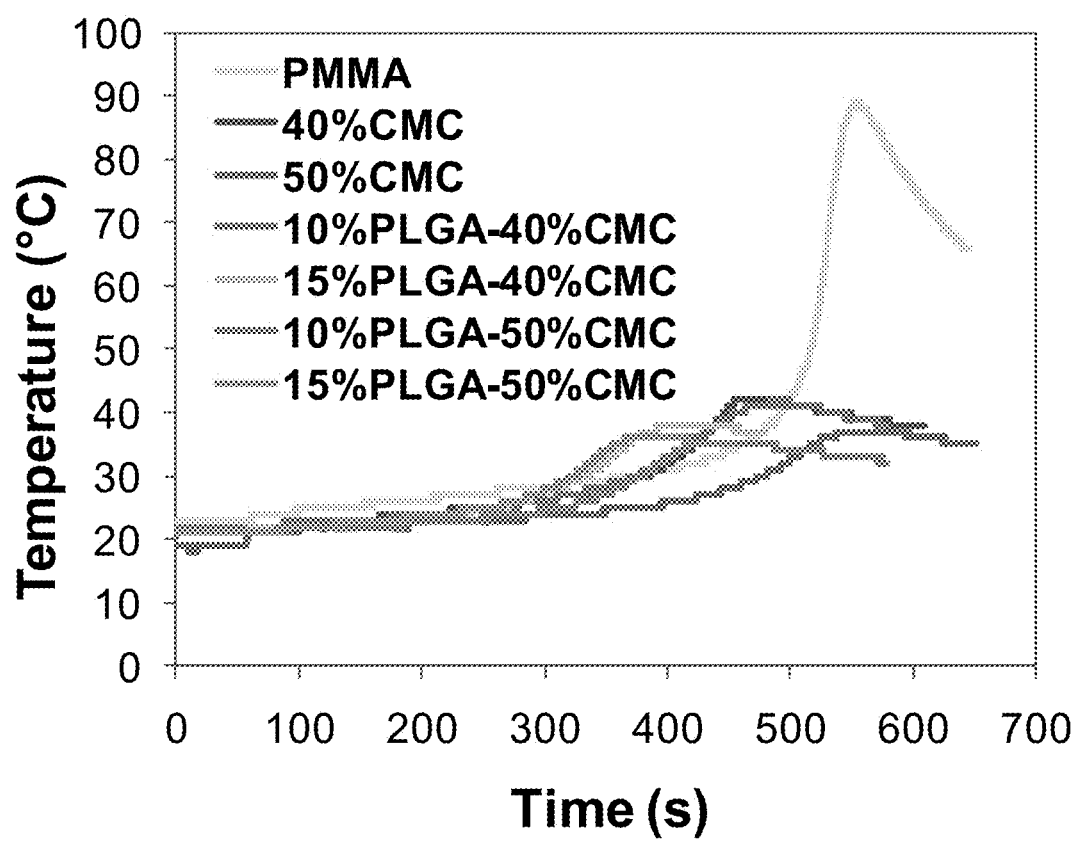
FIG. 10 is a representative graph of temperature change versus time during the setting process of PMMA, PMMA/CMC and PMMA/CMC/PLGA constructs.

The temperature change during the setting process was monitored following ISO5833 for acrylic cements to elucidate the influence of CMC/PLGA addition on the setting temperatures and times. Due to the exothermic nature of the PMMA/MMA polymerization reaction, the temperature in the pure PMMA cement rapidly increased to 88.3±0.6° C. Notably, CMC hydrogel incorporation significantly reduced the maximum temperature of constructs (FIG. 10 and Table 4). When incorporating CMC hydrogel alone, the maximum temperature was reduced to 43.7±2.1° C. for the 40 wt % CMC incorporation and 36.3±1.2° C. for the 50 wt % CMC incorporation (compared to 88.3±0.6° C. for the solid PMMA) ($p<0.05$). Importantly, higher CMC incorporation resulted in significantly greater reduction in the maximum temperature ($p<0.05$). The addition of PLGA besides CMC further reduced the maximum temperature in the 15% PLGA-40% CMC construct (38.7±1.2° C. versus 43.7±2.1° C. for the 40 wt % CMC-incorporating construct without PLGA) ($p<0.05$), whereas it did not alter the maximum temperatures ($p>0.05$) in other constructs. The setting times of PMMA/CMC or PMMA/CMC/PLGA constructs were reduced ($p<0.05$) by the presence of CMC hydrogel and/or PLGA microspheres except in the construct with 50 wt % CMC incorporation alone (Table 4).

TABLE 4

Maximum temperature, setting temperature and setting time of various constructs examined

| Constructs | Maximum temperature (° C.) | Setting temperature (° C.) | Setting time (min) |
| --- | --- | --- | --- |
| PMMA | 88.3 ± 0.6 | 55.3 ± 0.8 | 8.4 ± 0.5 |
| 40% CMC | 43.7 ± 2.1 | 32.3 ± 1.0 | 6.7 ± 0.1 |
| 10% PLGA-40% CMC | 39.3 ± 2.5 | 29.8 ± 1.0 | 6.2 ± 0.8 |
| 15% PLGA-40% CMC | 38.7 ± 1.2 | 29.8 ± 0.6 | 5.4 ± 0.2 |
| 50% CMC | 36.3 ± 1.2 | 28.3 ± 1.0 | 7.7 ± 0.3 |
| 10% PLGA-50% CMC | 34.0 ± 1.0 | 27.5 ± 0.5 | 5.7 ± 0.5 |
| 15% PLGA-50% CMC | 34.7 ± 1.5 | 28.0 ± 0.5 | 5.3 ± 0.2 |

Figure 11:
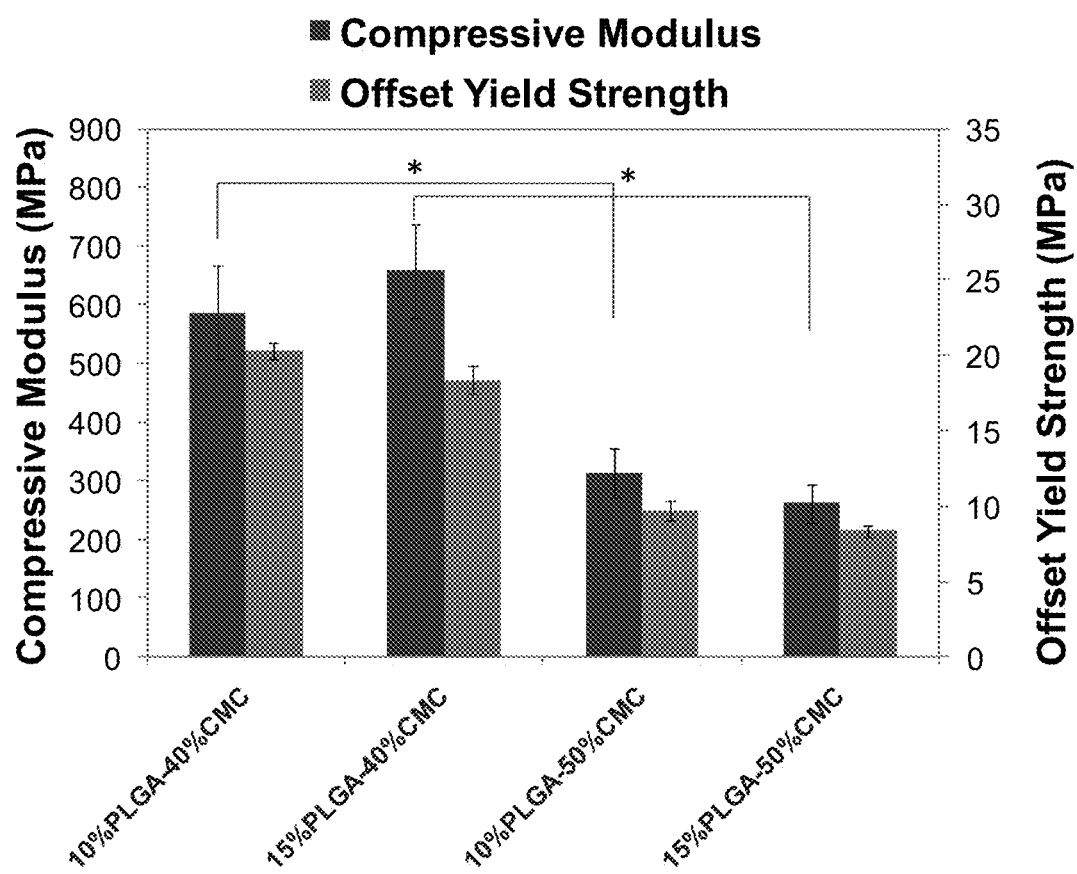
FIG. 11 is a graph depicting compressive modulus and offset yield strength of PMMA/CMC/PLGA constructs. Error bars represent standard deviation for n=6 and statistical significance ($p<0.05$) between relevant groups is denoted by *.

The compressive modulus and offset yield strength (2.0% offset) were determined based on ISO5833 (FIG. 11). The compressive modulus of porous PMMA/CMC/PLGA constructs varied between 262±33 and 658±80 MPa depending on the amount of CMC incorporation, and was lower than that of solid PMMA (2666±218 MPa) ($p<0.05$). The compressive mechanical performance was affected by the amount of CMC hydrogel incorporation, with greater CMC incorporation resulted in significantly lower compressive modulus (586±80-658±80 MPa for the 40 wt % CMC incorporation versus 262±33-313±41 MPa for the 50 wt % CMC incorporation) ($p<0.05$). The offset yield strength of PMMA/CMC/PLGA constructs presented a similar CMC-incorporation dependence ($p<0.05$).

Degradation Behavior of PMMA/CMC/PLGA Constructs

Construct formulations (cylinders 6 mm in height and 10 mm in diameter) that were designed for implantation within a recently developed rabbit mandibular defect model were degraded over a period of 12 weeks in vitro, and the degradation process was characterized by the changes in the bulk porosity and pore interconnectivity (FIG. 12) and compressive mechanical performance (FIG. 13). The crosssectional morphologies of constructs (FIG. 12A) demonstrated significant porosity and interconnectivity among pores of constructs in the different degradation stages. FIGS. 12B and 12C illustrate the quantitative increase of porosity and interconnectivity over the degradation process of 12 weeks. The PMMA/CMC/PLGA constructs initially featured a relatively low bulk porosity (5.9±3.8-8.0±7.0% for the 40 wt % CMC incorporation and 14.7±5.4-20.8±0.9% for the 50 wt % CMC incorporation at day 0). The bulk porosity increased significantly after the first day of degradation in the construct 15% PLGA-40% CMC (17.6±2.4%), 10% PLGA-50% CMC (32.4±1.2%) and 15% PLGA-50% CMC (36.9±3.0%) ($p<0.05$), but did not change significantly in the construct 10% PLGA-40% CMC (12.1±3.9%) ($p>0.05$). The bulk porosity exhibited an increasing trend over the degradation process of 12 weeks, reaching a plateau of 20.7±0.6-26.1±3.8% and 46.5±2.7-53.9±1.3% for the 40 and 50 wt % CMC incorporation, respectively (FIG. 12B). Notably, the formulations fabricated with greater CMC incorporation (50 wt %) possessed significantly higher porosity during the degradation process, and their porosity increased significantly after 12 week degradation ($p<0.05$); nevertheless, with the same CMC incorporation, the constructs with 10 and 15 wt % PLGA incorporation possessed similar porosities at the various stages of degradation. Similar CMC-incorporation dependence was also found in the pore interconnectivity of PMMA/CMC/PLGA constructs (FIG. 12C): the constructs with higher CMC hydrogel incorporation exhibited higher pore interconnectivity ($p<0.05$) at smaller minimum connection sizes after the first day degradation (the dependence of pore interconnectivity on CMC hydrogel incorporation at different degradation stages was similar; data not shown). For example, at 40 μm connection size, 62.0±4.8-72.6±3.8% of the pores inside the 50 wt % CMC-incorporating construct were interconnected through openings, whereas the interconnectivity in the construct with lower CMC incorporation was significantly less (20.5±7.9-29.8±7.2% at 40 μm connection size) ($p<0.05$).

Constructs of cylindrical form with dimensions of 6 mm in height and 10 mm in diameter were tested mechanically to determine the influence of CMC/PLGA degradation on compressive mechanical properties and to provide predictive insight into the expected mechanical performance of the constructs over time in vivo. The compressive modulus declined to 39.4±0.7-77.0±6.5% of the original compressive modulus after the first day of degradation and 12.2±2.0-32.0±2.0% after 12 weeks (FIG. 13). The decrease in compressive modulus after 12 weeks was significantly greater than that after the first day of degradation for the same construct ($p<0.05$). Notably, the construct with both higher CMC and PLGA incorporation (15% PLGA-50% CMC) processed the greatest reduction in compressive modulus after 12 weeks ($p<0.05$).

In Vitro Colistin Release

A 35-day in vitro release study was conducted to characterize the release kinetics of colistin. The PMMA/CMC/PLGA constructs exhibited triphasic release profiles similar to PLGA microspheres: an initial burst (17.5±0.9-24.0±0.7% per day at days 0-2), moderate release lag phase (0.5±0.0-0.9±0.0% per day at days 2-15), and sustained release periods (0.6±0.1-3.4±0.2% per day at days 15-28) (FIG. 14A and Table 5). Incorporating PLGA microspheres into PMMA constructs significantly reduced the initial release at the first day (23.0±1.5-32.8±1.9% for the PMMA/CMC/PLGA constructs versus 45.9±2.9% for the PLGA microspheres) ($p<0.05$), whereas the lag phase lasted longer for the PMMA/CMC/PLGA constructs (days 2-15 for the PMMA/CMC/PLGA constructs versus days 2-11 for the PLGA microspheres). Notably, the colistin release from the PMMA/CMC/PLGA constructs continued for another week (phase 4) after the accelerated, sustained release phase (0.6±0.1-1.0±0.3% and 1.8±0.3-1.9±0.7% colistin release for the 40 and 50 wt % CMC-incorporating constructs, respectively, during the fifth week) versus little or no colistin release after 4 weeks for the PLGA microspheres alone. All PMMA/CMC/PLGA constructs achieved considerable colistin release after 5 weeks (68.1±3.3-88.3±5.8%). The constructs prepared with higher CMC incorporation featured significantly greater amounts of colistin release for the same PLGA incorporation (85.4±7.2-88.3±5.8% versus 68.1±3.3-70.7±5.5%) ($p<0.05$) (Table 5), whereas varying PLGA microsphere incorporation did not significantly alter the total drug release for the same CMC incorporation ($p>0.05$). In terms of the release rate at the sustained release phase 3, increasing either the CMC or the PLGA incorporation resulted in significantly higher release during this period ($p<0.05$) (Table 5).

TABLE 5

Release rates of different phases of colistin release from microsphere-incorporating constructs

| PMMA/CMC/PLGA constructs | Phase 1 (day 0-2) (%/day) | Phase 2 (day 2-15) (%/day) | Phase 3 (day 15-28) (%/day)* | Phase 4 (day 28-35) (%/day) | Cumulative release (%) |
|---|---|---|---|---|---|
| 10% PLGA-40% CMC | 24.0 ± 0.7 | 0.9 ± 0.0 | 0.6 ± 0.1 | 0.1 ± 0.0 | 68.1 ± 3.3[#] |
| 10% PLGA-50% CMC | 22.4 ± 1.2 | 0.5 ± 0.0 | 2.5 ± 0.4 | 0.3 ± 0.0 | 85.4 ± 7.2[#] |
| 15% PLGA-40% CMC | 19.2 ± 1.0 | 0.7 ± 0.0 | 1.7 ± 0.2 | 0.1 + 0.0 | 70.7 ± 5.5[##] |
| 15% PLGA-50% CMC | 17.5 ± 0.9 | 0.6 ± 0.1 | 3.4 ± 0.2 | 0.3 ± 0.1 | 88.3 ± 5.8[##] |

*In the phase 3 release rates, all groups are statistically different ($p < 0.05$).
[#,##]indicate the statistical significance ($p < 0.05$) between the cumulative release of 10% PLGA-40% CMC and 10% PLGA-50% CMC, and the cumulative release of 15% PLGA-40% CMC and 15% PLGA-50% CMC.

FIG. 14B presents the release rate of colistin (i.e., the average concentration of released colistin per day), providing insight into the immediate local drug concentration throughout the release period. The daily release varied in accordance with the colistin release rate at different release phases. During the release period of 5 weeks, the concentration of released colistin within/around the construct remained at a level much higher than or around 10 μg/mL. For example, at the lowest point of lag phase of day 15, the constructs released colistin at a concentration of 16.6±8.4-42.3±7.5 μg/mL.

Discussion

Space maintenance, as the initial stage of a two-stage regenerative medicine approach toward reconstructing large bony defects, is particularly attractive when immediate reconstruction is not indicated (e.g., tumor margin verification, infected wound sites, lack of soft tissue coverage, and regenerative material not immediately available). An implant with the desirable characteristics of PMMA with additional features such as improved incorporation into the surrounding tissue bed would be ideal. A porous PMMA structure induced by the CMC hydrogel addition was designed in this example to promote tissue healing and material retention by allowing for tissue ingrowth into the surface pores. Furthermore, a colistin releasing strategy (i.e., colistin-releasing particulate PLGA) was incorporated to eliminate infection-associated complications during the space maintenance phase and later reconstruction.

Figure 8:
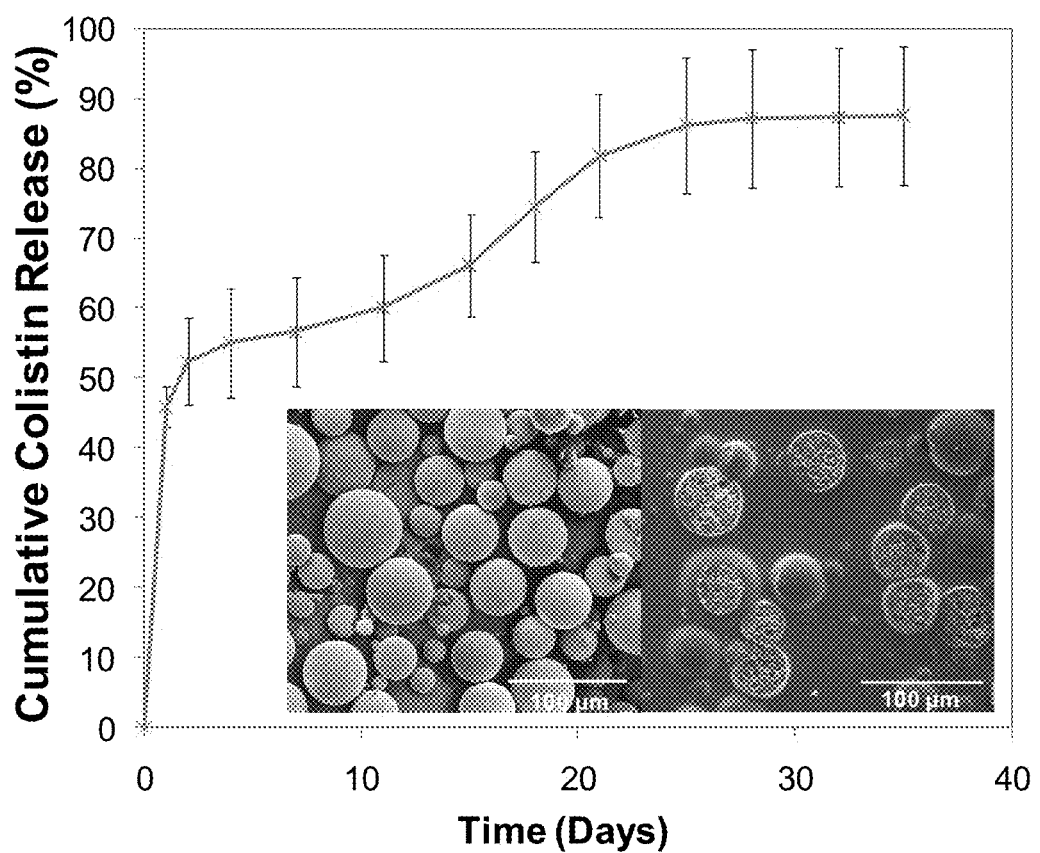

The colistin release profile presented in FIG. 8 illustrates a typical degradation-controlled release pattern: the initial burst is the rapid release of surface-associated drugs; the lag phase of moderate drug release reflects the time necessary for PLGA hydrolysis to a critical chain length to allow dissolution and release of entrapped drug; and a sustained, accelerated drug release is followed where pore formation and fragmentation of the microspheres enhance erosion-accelerated drug release. As the first attempt of controlled delivery of colistin from PLGA, the 4-week continuous release demonstrated the suitability of PLGA microspheres as drug carrier for colistin. To fabricate a colistin-releasing porous PMMA construct, CMC hydrogel and PLGA microspheres were co-incorporated into a clinically used PMMA cement. Physically mixing all components (PLGA microspheres, PMMA powder, CMC hydrogel and MMA monomer) prior to MMA polymerization is an appealing method that could be used intraoperatively to create a porous construct with PLGA microspheres homogeneously entrapped within the polymer phase (FIG. 9). The aqueous CMC hydrogel micro-coalescences were dispersed throughout the curing material, creating a filament network (FIG. 9). Resorption of the inclusions by the aqueous environment left voids forming the pore structure (FIG. 12). The incorporation of CMC hydrogel created immediate surface/bulk porosity after fabrication. The degradation of PMMA/CMC/PLGA constructs (due to the dissolution of CMC and PLGA as well as any PMMA cement erosion upon contact of the construct with the aqueous/biological environment) generated further porosity throughout the constructs (FIG. 12). By varying the PLGA and CMC composition, the PMMA/CMC/PLGA constructs featured both low (12.1±3.9-26.1±3.8% created by the 40 wt % CMC incorporation) and high (32.4±1.2-53.9±1.3% created by the 50 wt % CMC incorporation) porosity initially and throughout the degradation process, which matched the porosity of previously evaluated PMMA/CMC constructs (16.9% or 44.6% porosity). Those porous PMMA/CMC constructs improved oral mucosal healing as compared to non-porous PMMA over a clean/contaminated bone defect created in the rabbit mandible.

Besides imparting immediate porosity, an additional advantage offered through CMC incorporation was a substantial reduction of the setting temperature (FIG. 10 and Table 4). The high temperature attained by exothermic polymerization of conventional PMMA cements has largely limited the types of antibiotics effectively incorporated into the cement. With the CMC hydrogel acting as an efficient heat sink and the CMC/PLGA addition "diluting" the polymerization (relatively less monomer polymerizes per unit volume), the PMMA/CMC/PLGA formulations produced maximum temperatures close to the physiological temperature of 37° C. This allows the loaded constructs to cure in vivo with little potential for thermal damage to sensitive antibiotic drugs or surrounding cells and tissues.

The creation of a porous structure, however, led to an expected and undesirable decline in the compressive mechanical properties relative to solid PMMA (FIG. 11), in accordance with the typical porosity-mechanical property relationship in scaffold materials. The decrease in compressive properties (262±33-658±80 MPa original compressive modulus; the compressive mechanical property declined further over time with construct degradation and subsequent bulk porosity increase) (FIG. 11-13) presents a compromise if the construct is to be used for load-bearing applications, especially when long-term mechanical support (e.g., weeks or months) is required. For application in the craniofacial complex, porous PMMA constructs with significant porosity (50 vol %) remain useful in correcting craniofacial contour deformities and repairing defects in clinical applications, so even after 12 weeks of degradation (where the porosity of the PMMA/CMC/PLGA constructs did not exceed 50%), the PMMA/CMC/PLGA implants hold promise in providing support of craniomaxillofacial structures. As shown in Example 1, PMMA/CMC implants with 16.9% and 44.6% porosity were able to maintain mandibular space over 12 weeks with no signs of collapse or mechanical compromise visible. In addition, the amount of CMC incorporation primarily determined the physical properties of the PMMA/CMC/PLGA constructs (i.e., decreased CMC incorporation resulted in increased mechanical strength), making it feasible to tune the balance between porosity and subsequent drug release with the mechanical properties to meet a specific need of space maintenance/drug delivery.

In these PMMA/CMC/PLGA constructs, the original porosity and the porosity change over time would consequently impact the progressive tissue ingrowth (as in an in vivo environment), mechanical performance, and most importantly, drug elution through the open paths. The investigation of these properties throughout construct degradation will help to predict their capacity to allow tissue to integrate and correlate drug release kinetics with the porosity characteristics of the construct. As seen in FIG. 12B, the significant increase in the bulk porosity after the first day of degradation could be mainly attributed to the rapid dissolution of CMC to the surrounding aqueous environment. This immediate porosity will be essential for the initial tissue ingrowth since it is during the first 7 days after implantation that extensive invasion of vascularised fibrous connective tissue into surface pores occurs. The continuous CMC/PLGA dissolution created further porosity over a period of 12 weeks (FIG. 12B), which will potentially allow for the further integration of soft tissue or even the gradual ingrowth of hard tissue, promoting the formation of a stronger interface between the tissue and material. In addition, the development of the porosity was slow which will help to prevent early bacterial seeding of the implants, a development which potentially caused an inflammatory reaction in response to more porous formulations of PMMA/CMC implants tested in vivo in a clean/contaminated wound model.

Importantly, the surface/bulk porosity characteristics of PMMA/CMC/PLGA constructs was predominantly controlled by the CMC incorporation (FIG. 12B) (i.e., the higher the CMC incorporation, the greater the surface/bulk porosity and pore interconnectivity). With respect to the concept of anchoring the constructs by tissue ingrowth into the surface pores, the degree of tissue ingrowth depends on the degree of surface porosity (the greater the pore size and interconnectivity, the greater the tissue penetration) and dictates the strength of tissue-material interfaces. The tunable surface/bulk porosity of the PMMA/CMC/PLGA constructs allows for the preparation of constructs with different degrees of porosity and the use of these constructs in applications at a wide range of sites where various strengths of the tissue-porous implant interface are expected.

The rapid dissolution of CMC yielded initial porosity and allowed fluid to penetrate into the inner phase of the construct to initiate PLGA hydrolysis and subsequent drug release. The CMC/PLGA dissolution generated more open paths, which largely benefited the drug elution from the inner structure of the constructs. The impact of bulk porosity and pore interconnectivity on the drug release was confirmed by the significantly higher drug release rate and total amount of released drug (Table 5) achieved by the constructs with 50 wt % CMC incorporation (which possessed the higher porosity and more extensive pore interconnectivity). The colistin release from the PMMA/CMC/PLGA constructs achieved a prolonged release duration (5 weeks) and significantly enhanced cumulative release (68.1±3.3-88.3±5.8%) (FIG. 14A) relative to those reported for solid or porous PMMA constructs. Existing antibiotic-releasing PMMA formulations, where antibiotic drugs are directly mixed into the cement, usually feature a poor drug elution profile consisting of a large initial burst release followed by an ineffective slow release over days or weeks. The nondegradable polymer entraps medications in its inner domain with limited accessibility to the exterior for drug diffusion, thus leading to incomplete release of entrapped antibiotics. Although the release kinetics can be improved by creating additional elution mechanisms (such as increasing drug loading or incorporating solid porogens to induce porosity), the resulting enhancement in the total amount of drug released is not significant (10-20%). The PMMA/CMC/PLGA constructs described here overcome the problems associated with existing antibiotic-releasing PMMA cements resulting in extended periods of high drug concentration and nearly complete drug release. In these PMMA/CMC/PLGA constructs, both the CMC and the PLGA incorporation play essential roles in improving drug release: the rapid CMC dissolution creates open paths for fluid penetration to initiate PLGA polymer hydrolysis; the gradual PLGA degradation controls drug release for a prolonged period and creates further paths for more complete drug release. Eliminating either the PLGA or CMC component did not yield improved drug release, as our previous experiences demonstrated that PLGA microsphere-incorporating solid PMMA constructs (without CMC to impart porosity) exhibited a low initial burst with little or no further release due to the lack of open paths for polymer degradation and drug dissolution; drug-incorporating porous PMMA/CMC constructs (without PLGA microspheres loaded with drugs) exhibited a large initial burst with little or no further release due to the lack of a controlled release mechanism (data not shown).

Notably, the daily colistin release from the PMMA/CMC/PLGA constructs remained at a relatively high level considering that colistin exhibits excellent activity against susceptible species with reported minimum inhibitory concentrations (MICs) of 0.5-5 µg/mL. The released colistin presumably created a local concentration well exceeding its inhibitory concentration (e.g., 33-84 fold higher than the MIC of colistin against *Acinetobacter baumannii* at the lowest point of lag phase of day 15) during the release period of 5 weeks (FIG. 14B). Antibiotic release at a concentration significantly greater than the MIC has great potential for rapid bacterial clearing. For these PMMA/CMC/PLGA constructs, both the amount of drug release and the release duration meet the criteria of efficient local antibiotic delivery.

This example suggested that impregnating PLGA microspheres into PMMA porous constructs resulted in a similar release pattern as that of PLGA microspheres alone (with slightly changed total release and release duration which can be also tuned by the weight percentages of CMC and PLGA incorporated). Potentially, the PMMA/CMC/PLGA constructs described in this example can serve as a platform of drug-releasing porous implant materials for a wide range of drug delivery applications (e.g., other than antibiotic delivery for infection control, growth factors can be controlled delivered via these constructs to prime the wound site), where the pre-designed drug-releasing PLGA microspheres can be readily impregnated into porous PMMA constructs and a desired drug release pattern (including the release duration, release rate, and total release amount) can be further manipulated by modifying the weight percentages of CMC and PLGA incorporated.

EXAMPLE 3

In this example, the effect of in situ formed porous PMMA implants versus solid implants was tested. Previous studies have produced prefabricated implants, such that molds and pre-implantation testing could be utilized for greater control of experimental parameters. In clinical practice, these materials will not be used in such a manner, as the advantage of materials such as PMMA space maintainers is their ability to be formed and shaped intraoperatively to fit a wide range of defect sizes and shapes. This comparison is essential to the preclinical testing as the surface characteristics, which have been attributed to the porous material's success in soft tissue coverage, is less controlled when the implant is formed by hand versus by a mold.

Experimental Design

This example included two groups, a solid and a porous group, using the porous formulation found to be optimal from the above examples, where the aqueous gel consists of 9 wt % CMC and composes 30 wt % of the entire implant with specific masses as shown in Table 6.

TABLE 6

Component Weights for Solid and Porous PMMA Space Maintainers.

| Component | Solid Implant | Porous Implant |
|---|---|---|
| CMC Gel | 0 g | 0.3 g |
| Bone Cement Powder | 0.679 g | 0.475 g |
| Bone Cement Monomer | 0.321 g | 0.225 g |

These implants were implanted into a 1 cm diameter bicortical defect in the body of the mandible as shown in FIG. 15. Additionally, this model included a 2-3 mm notch in the superior border of the defect also shown in FIG. 15. This notch, with the removal of the overlying tooth, allowed for communication between the defect and the oral cavity to expose the defect to saliva fluids and bacteria to more correctly simulate a traumatic defect. Additionally, this model provided a measure of the healing capacity of the soft tissue over the surface of the implant.

Material and Methods

Materials

High Viscosity SmartSet Bone Cement (Depuy Orthopaedics, Warsaw, Ind.) was used as is and was provided in sterile packaging. Carboxymethylcellulose (Spectrum Manufacturing Corp., Gardena, Calif.) was sterilized as a powder in a thin layer under UV light for 30 min.

Implant Preparation

CMC was dissolved in sterile water at 9 wt % by sonication in ice water. The resulting CMC gel and powder and monomer phase of the bone cement was weighed sterilely to produce implants with volumes of 0.471 mL (corresponding to the volume of the defect) as shown in Table 6 and placed in separate vials for mixing intraoperatively.

During intraoperative mixing, solid samples were prepared by thoroughly mixing the powder component with the liquid component of the bone cement. For porous implants the powder component of the bone cement was first added to the CMC gel and mixed well. The liquid component of the bone cement was added to that mixture and again mixed well. After mixing, the samples were removed from the vials when their consistency was doughy and no longer tacky, corresponding to approximately 5 minutes after addition of the monomer. The material was then shaped to fit inside the defect.

Surgical Procedure

Solid and porous PMMA implants were evaluated in vivo in a modified rabbit mandibular defect model as previously described above. All procedures followed the protocol approved by the Institutional Animal Care and Use Committees at Rice University and University of Texas Health Science Center at Houston and the Animal Care and Use Committee of the Department of Defense. Twenty-two New Zealand white rabbits (n=10 per group, with 2 euthanized early) at least 6 months old and weighing 3.5-4 kg were purchased from Myrtle's Rabbitry (Thompson Station, Tenn.).

Briefly, each animal was given preoperative intramuscular doses of buprenorphine hydrochloride (0.1 mg/kg body weight) for postoperative analgesia and 0.5 mL Durapen (150,000 U/mL penicillin G benzathine and 150,000 U/mL penicillin G procaine) for perioperative antibiotic coverage. Before induction, ketamine hydrochloride (40 mg/kg body weight) and xylazine hydrochloride (7.5 mg/kg body weight) were given, after which rabbits were placed in a supine position, intubated, and placed under general anesthesia using an isoflurane-$O_2$ mixture (2.5%-3% isoflurane for induction, 2% for maintenance) with constant cardiac and respiratory monitoring. The animals were then surgically prepped and draped, after which a 7-cm midline incision through the skin and superficial fascia was made beginning 0.5 cm posterior to the mentum. Using blunt dissection and electrocauterization, the masseter was exposed and the soft tissue along the inferior border of the body of the hemimandible was mobilized such that the periosteum covering the body of the mandible could be incised and elevated, exposing a 4 cm by 1.5 cm area on the lateral surface of the mandible. A 10-mm titanium trephine (Ace Surgical Supply, Inc., Brockton, Mass.) attached to a Stryker TPS surgical handpiece (Stryker, Kalamazoo, Mich.) operating at 15,000 rpm with copious normal saline irrigation was used to create a bicortical defect through the exposed body of the right mandible. A 701 bur in combination with the surgical drilling unit was used to cut a 2-3 mm window through the alveolar ridge in the middle of the defect to provide access for removal of the crowns of the associated teeth and provide intraoral exposure of the defect. The defect site was thoroughly washed with normal saline, after which an implant was mixed as described above and placed within the defect. Before closure, a titanium supporting plate (1.5 mm six-hole heavy-gauge titanium; Synthes, West Chester, Pa.) was secured in place to prevent iatrogenic fracture during the course of the study. The incision was then closed in three layers (muscle, fascia, and skin) using degradable sutures (Vicryl polyglactin sutures; Ethicon, Somerville, N.J.). After wound closure, anesthesia was reversed, and the animals were extubated.

Postoperatively, the animals were given access to food and water ad libitum. Food was limited to a soft recovery diet (Critical Care for Herbivores; Oxbow Pet Products, Murdock, Nebr.) and shredded or mashed fruits and vegetables to reduce stress on the mandible for the entirety of the study. Two animals had skin incision infections and were given an extra dose of Durapen and the incisions were reopened superficially, washed thoroughly with normal saline, and closed again with Vicryl sutures. Both animals recovered well and required no further care beyond the standard protocol. One animal was euthanized per veterinary recommendation due to an unresolved foot infection resulting from nail removal in the animal's quarters. Another animal died before the time point due to abdominal infection from a perforated bowel. During necropsy, no signs indicated the surgical procedure or implant as a factor in the bowel perforation.

Gross Evaluation

Animals were euthanized at 12 weeks according to protocols approved by the IACUCs of Rice University and University of Texas Health Science Center at Houston and the Animal Care and Use Committee of the Department of Defense by an intravenous injection of 1 mL of Beuthanasia-D (390 mg/mL pentobarbital sodium and 50 mg/mL phenytoin sodium). The hemimandibles were then carefully dissected from the cranium with care taken to preserve the soft tissue surrounding the implant and within the oral cavity. The oral mucosa and dentition covering the alveolus of each specimen was examined to detect any areas of implant or bone exposure. Specimens were individually placed in 10% neutral buffered formalin and stored on a shaker table at 4° C. for 72 hours for fixation.

Histology

After fixation, samples were dehydrated, stored in 70% ethanol, and then embedded in MMA. After polymerization of the MMA, three coronally oriented 10-μM-thick sections through the center of each implant were cut using a modified diamond saw technique and subsequently stained using methylene blue/basic fuchsin. Each of the stained sections was analyzed using light microscopy (Zeiss Axio Imager Z1 and AxioCam MRc 5; Carl Zeiss AG, Oberkochen, Germany) by three blinded observers. The quantitative scoring system described above (Table 1) was used to score the tissue response at the implant interface and within the pores of the porous implants.

Statistical Analysis

Gross evaluation data was analyzed using Fischer's Exact Test. Histological scores was evaluated using Mann Whitney U-test. The a priori level of significance for both tests was chosen to be $\alpha=0.05$. All analyses were performed using MATLAB release 2010a (Natick, Mass.).

Results

Gross Evaluation

Similar trends to Example 1 were obtained in the studies examining gross healing and were not statistically significant as shown in FIG. 16.

Histology

Applying the scoring system in Table 1, the scores exhibited a distribution similar to Example 1. FIG. 17 shows the score of the tissues at the tissue implant interface and in the pores of the implant. The induced porosity exhibited no increased inflammatory response by the tissue.

EXAMPLE 4

Due to the complications of primary mandibular reconstruction, secondary reconstruction has advantages but with less satisfactory results due to loss of soft tissue and bone void space. In this case series, three patients diagnosed with ameloblastoma of the mandible underwent resection of the tumor and placement of a porous polymethylmethacrylate (PMMA) space maintainer. This space maintainer was fabricated by mixing the powder phase of bone cement (SmartSet HV, Depuy Orthopaedics or Cobalt HV, Biomet) with Surgiflo Hemostatic Matrix (Ethicon), where the weight of Surgiflo accounted for 30% of the entire implant. The monomer phase of the cement was added to this mixture and allowed to polymerize in situ or molded by hand or a silicone cast ex vivo, creating a porous PMMA material. The defects ranged in size from a 1.5×2.0 cm full thickness notch defect to two continuity defects 4.0 and 4.5 cm in length. All space maintainers were held in place with a titanium plate and screws. Two cases developed small lateral mucosal dehiscences; however these did not increase in size and maintained enough of the soft tissue envelope that oral surgical approaches were used to remove the space maintainer and place the bone graft. All three cases reported a metallic taste for the first 2-3 weeks of implantation. The space maintainers were explanted 8, 14 and 17 weeks postoperatively. Porous PMMA adequately maintained space and the soft tissue envelope for secondary mandibular reconstruction.

EXAMPLE 5

Antibiotic releasing porous space maintainers were evaluated in an infected rabbit mandibular composite tissue defect model. Temporal release and magnitude of release were varied to evaluate their effects on clearance of the infection, soft tissue healing and inflammatory response. Additionally the safety of the local delivery was measured via serum blood markers for kidney function and histology. Results showed an effect on gross soft tissue healing in response to temporal delivery changes and local delivery resulted in no decreased kidney function as measured by serum markers.

Infection control remains a critical aspect of all surgical manipulations, particularly those involving the implantation of a foreign body, where up to 42.6% of craniofacial reconstructions fail due to infection. Porous space maintainers can be used in bone/mucosa composite tissue defects to allow for soft tissue healing over the implant. Good soft tissue coverage primes the wound site for subsequent bone repair upon removal of the space maintainer. Additionally, porous space maintainers enable the controlled release of colistin, an antibiotic, in vitro. Colistin serves as an ideal candidate for local delivery, given its general clinical disuse systemically due to potential nephrotoxic effects. However, local delivery should minimize systemic exposure and thus reduce the toxic effect and allow a potent otherwise unused antibiotic to be used. This example evaluates the use of colistin-releasing porous polymethylmethacrylate space maintainers in a rabbit mandibular composite tissue defect model inoculated with a clinical isolate strain of *Acinetobacter baumannii*.

Experimental Methods

Implants were composed of a clinical grade bone cement comprised mostly of polymethylmethacrylate (PMMA), clinical grade gelatin, colistin or colistin loaded poly(DL-lactic-co-glycolic acid) (PLGA) microparticles. PLGA microparticles were fabricated using a double emulsion technique as previously described in Shi, M. et al. *J. Control. Release*. 152 (2011) 195-205. Four groups were tested as shown in Table 7 with 10 rabbits in each group. The in vitro release profiles from the four groups were selected such that the burst release from the Gelatin and PLGA High groups are the same for the first 7 days. The PLGA High group continued to release colistin subsequently while the Gelatin group did not. The PLGA Low group is half of the dose of the PLGA High group but with the same profile evaluating the dose effect. The Uninfected group contained the same formulation as the PLGA High groups without the inoculum.

TABLE 7

Group formulations indicating the controlled delivery vehicle, dose of antibiotic, and presence of inoculum.

| Group | Colistin Carrier | Colistin Dose | Inoculation | n |
|---|---|---|---|---|
| Uninfected | PLGA | 20 mg/defect | No | 10 |
| Gelatin | Gelatin | 15 mg/defect | Yes | 10 |
| PLGA Low | PLGA | 10 mg/defect | Yes | 10 |
| PLGA High | PLGA | 20 mg/defect | Yes | 10 |

A non-healing 1 cm diameter bicortical defect was created in the rabbit mandible with a 2-3 mm notch in the superior aspect of the defect where the overlying tooth was removed creating intraoral communication as well as a mucosal defect. The defects were inoculated with $2 \times 10^7$ colony forming units of a rabbit virulent strain of *A. baumannii* isolated from a deep wound of a soldier returning from Iraq. Subsequently, the colistin-loaded space maintainers were fabricated intraoperatively and implanted.

Serum levels of creatinine and blood urea nitrogen were measured at 1 and 5 weeks postoperatively to assess any nephrotoxicity of the locally delivered antibiotic. All 40 rabbits were euthanized at 12 weeks. At the time of euthanasia, blood, saliva and a swab of the defect were collected and cultured for the presence of *A. baumannii*. The mandibles and kidneys were harvested and fixed in formalin. The gross healing of the mucosal defect was noted for each mandible and the classifications were analyzed statistically with the Fisher's exact test.

Mandibular samples were sectioned and stained with methylene blue and basic fuchsin and the Brown-Hopps stain while kidney specimens were sectioned and stained with hematoxylin and eosin.

Results and Discussion

Serum levels of blood urea nitrogen and creatinine were normal for all rabbits at 1 and 5 weeks indicating no nephrotoxic effects of the delivery system. No blood or defect swabs cultured were positive for *A. baumannii*, and 37 of 40 saliva swabs cultured have been negative for *A. baumannii* as well. Three cultures remain to be tested for the presence of the strain. The negative cultures indicate clearance of the infection.

Gross healing was classified as well-healed or non-healed referring to the oral mucosa defect. Well-healed specimens showed complete coverage of soft tissue with no exposure of the implant or fistulas. Non-healed specimens failed to cover the implant where the initial mucosal defect was. Additionally separate dehiscences were noted and specimens were classified as with or without a dehiscence. FIG. 18 shows the results with a significant difference in defect healing between the gelatin loaded and high dose PLGA groups.

This difference indicates that antibiotic delivery affected healing and although there was no difference between the low and high doses of colistin released the lower dose may have been slower to clear the infection and resulted in less healing.

Representative histological images are shown in FIG. 19, however histological scores of the tissue response have yet to be completed.

The local delivery of colistin was safely administered to rabbit mandibles inoculated with *A. baumannii*. The infection was cleared, and while contribution by the antibiotic delivery cannot be fully determined, the delivery of antibiotic affected gross healing of the defect.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method for maintaining a void in an osseous defect in a subject comprising:
    applying a temporary space maintenance composition to the void in the osseous defect, wherein the temporary space maintenance composition comprises polymethylmethacrylate and a porogen, and wherein the temporary space maintenance composition has a porosity from about 10% to about 30%; and
    removing the temporary space maintenance composition from the void to permit subsequent application of a tissue construct to the void.

2. The method of claim 1 wherein the temporary space maintenance composition further comprises an antibiotic.

3. The method of claim 2 wherein the antibiotic is present in a microparticle comprising poly(lactic-co-glycolic acid).

4. The method of claim 1 wherein the temporary space maintenance composition further comprises a bioactive factor.

5. The method of claim 4 wherein the bioactive factor is present in a microparticle comprising poly(lactic-co-glycolic acid).

6. The method of claim 1 wherein the temporary space maintenance composition comprises surface pores having a diameter of from about 50 µm to about 150 µm.

7. The method of claim 1 wherein the removing step is performed more than a month after applying the temporary space maintenance composition to the void.

8. The method of claim 1 wherein the tissue construct is bone.

9. The method of claim 1 wherein the osseous defect is in the subject's craniofacial region.

* * * * *